(12) United States Patent
Johnson

(10) Patent No.: US 7,733,488 B1
(45) Date of Patent: Jun. 8, 2010

(54) COMPACT MULTI-WAVELENGTH OPTICAL READER AND METHOD OF ACQUIRING OPTICAL DATA ON CLUSTERED ASSAY SAMPLES USING DIFFERING-WAVELENGTH LIGHT SOURCES

(75) Inventor: Lyle C. Johnson, Burlington, VT (US)

(73) Assignee: Revolution Optics, LLC, Burlington, VT (US)

( * ) Notice: Subject to any disclaimer, the term of this patent is extended or adjusted under 35 U.S.C. 154(b) by 257 days.

(21) Appl. No.: 12/020,900

(22) Filed: Jan. 28, 2008

Related U.S. Application Data

(60) Provisional application No. 60/886,797, filed on Jan. 26, 2007, provisional application No. 60/979,255, filed on Oct. 11, 2007.

(51) Int. Cl.
*G01J 3/51* (2006.01)
(52) U.S. Cl. .................. 356/414; 356/419; 356/420
(58) Field of Classification Search .................. 356/414, 356/419, 420
See application file for complete search history.

(56) References Cited

U.S. PATENT DOCUMENTS

| | | | |
|---|---|---|---|
| 3,910,701 A | 10/1975 | Henderson et al. | |
| 4,240,751 A | 12/1980 | Linnecke et al. | |
| 4,591,550 A | 5/1986 | Hafeman et al. | |
| 5,073,029 A | 12/1991 | Eberly et al. | |
| 5,112,134 A | 5/1992 | Chow et al. | |
| 5,545,531 A | 8/1996 | Rava et al. | |
| 6,043,880 A | 3/2000 | Andrews et al. | |
| 6,151,111 A | 11/2000 | Wechsler et al. | |
| 6,297,018 B1 | 10/2001 | French et al. | |
| 6,828,109 B2 | 12/2004 | Kaplan | |
| 6,982,431 B2 | 1/2006 | Modlin et al. | |
| 6,995,844 B2 | 2/2006 | Hafeman et al. | |
| 7,170,597 B1 | 1/2007 | Hooper et al. | |
| 7,199,377 B2 | 4/2007 | Wulf et al. | |
| 2005/0122521 A1 | 6/2005 | Katzlinger et al. | |
| 2005/0124013 A1 | 6/2005 | Bonen et al. | |
| 2006/0210962 A1 | 9/2006 | Imaizumi et al. | |
| 2007/0183931 A1 | 8/2007 | Stock et al. | |
| 2007/0231821 A1 | 10/2007 | Bupp et al. | |

FOREIGN PATENT DOCUMENTS

| | | | |
|---|---|---|---|
| EP | 172892 B1 | | 7/1991 |
| JP | 4132960 A | | 5/1992 |
| JP | 6174635 A | | 6/1994 |
| JP | 2005-9876 | * | 1/2005 |

* cited by examiner

*Primary Examiner*—F. L Evans
(74) *Attorney, Agent, or Firm*—Downs Rachlin Martin PLLC

(57) ABSTRACT

An optical reader having an array of differing-color light sources and a controller for controlling the light sources and acquisition of optical data. The light sources are arranged, and the controller is configured, to allow rapid acquisition of optical data regarding individual sample wells of a cluster of such wells. In some embodiments, multiple ones of the differing-color light sources are illuminated simultaneously for acquiring optical data on a corresponding number of sample wells. Depending on the configuration of the array and number of differing-color light sources illuminated simultaneously, the optical reader can acquire optical data for several wavelengths in a fraction of the time of conventional optical readers. Other embodiments include one or more non-contact temperature sensors for acquiring temperature data substantially simultaneously with the optical data. The temperature data can be used, for example, to adjust the optical data or warn a user of out-of-specification temperature conditions.

20 Claims, 18 Drawing Sheets

Electronic Block Diagram

FIG. 17
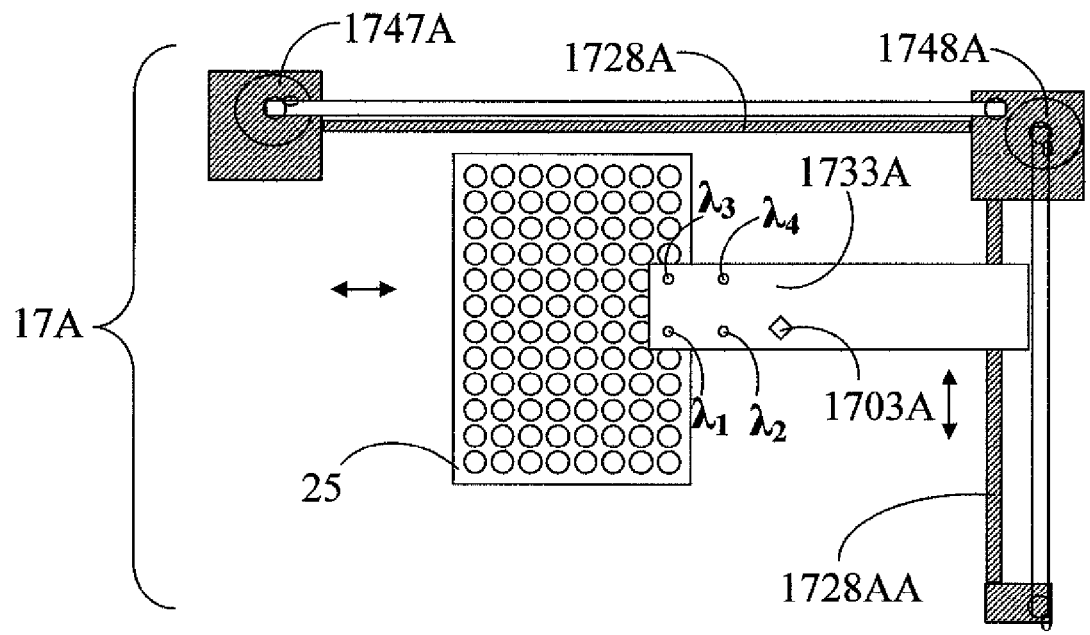
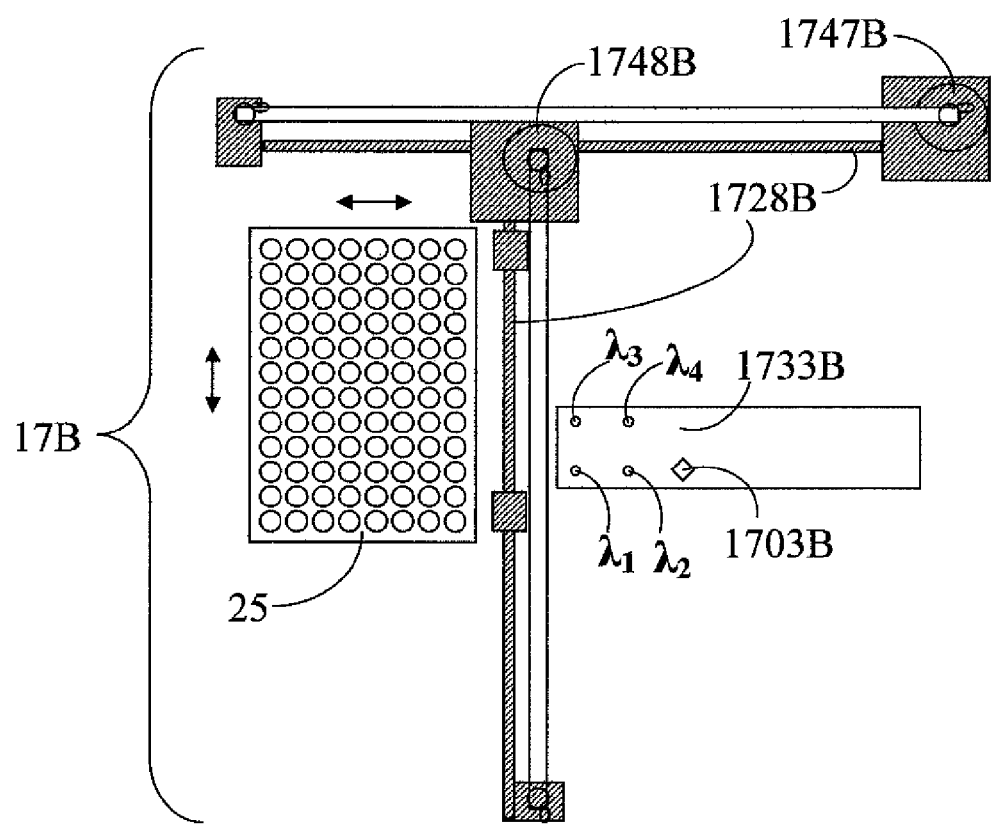

COMPACT MULTI-WAVELENGTH OPTICAL READER AND METHOD OF ACQUIRING OPTICAL DATA ON CLUSTERED ASSAY SAMPLES USING DIFFERING-WAVELENGTH LIGHT SOURCES

RELATED APPLICATION DATA

This application claims the benefit of priority of U.S. Provisional Patent Application Ser. No. 60/886,797, filed on Jan. 26, 2007, and titled "Compact, Maintenance-Free Multi-Wavelength Microplate Absorbance Reader," and U.S. Provisional Patent Application Ser. No. 60/979,255, filed on Oct. 11, 2007, and titled "Compact, Maintenance-Free Multi-Wavelength Microplate Absorbance Reader," each of which is incorporated herein in its entirety.

FIELD OF THE INVENTION

The present invention generally relates to the field of analytical light absorption measuring equipment. In particular, the present invention is directed to a compact multi-wavelength optical reader and method of acquiring optical data on clustered assay samples using differing-wavelength light sources.

BACKGROUND

Measuring the light absorption of a chemical solution is a useful means for detecting and measuring chemicals of interest in the fields of biochemistry, medical diagnostics, and other fields of scientific research. Scientists commonly use the "microplate" as a vessel for holding an array of samples while measuring, or "reading," their absorption. Microplates typically meet the American National Standards Institute (ANSI) standards developed by The Society for Biomolecular Sciences (SBS) (Danbury, Conn.). These standards describe microplate dimensions in detail including the common 3.3" by 5" microplate of 96 sample wells arranged in an 8 by 12 array with an on-center separation of 9.0 millimeters (mm). SBS has formalized ANSI standards for a 384-well microplate (on-center well separation of 4.5 mm) and 24-well microplates (on-center well separation of 18 mm) while other geometries such as 12-well and 48-well plates exist that may not have ANSI standards.

Scientists find it desirable to be able to perform multiple tests on a sample in the same microplate or in the same well of a microplate, for example, in screening blood samples for multiple drugs of abuse. By combining tests on the microplate, the scientist requires a smaller sample volume, consumes less chemical reagents and fewer microplates, and generates less waste. In addition, the scientist may benefit from an overall reduction in preparation time compared to the time required to prepare multiple single-test microplates. Tests can only be combined in the same well if they utilize different reading wavelengths; otherwise, different test results are indistinguishable from one another.

While microplates provide a convenient method of holding a large number of samples, generally, conventional microplate readers and methods for measuring the optical absorption of these samples have one or more shortcomings. For example, several known readers can read at only a single wavelength. Other known microplate readers can read at multiple wavelengths but they cannot perform multiple wavelength-reads simultaneously, increasing the time for each wavelength reading by approximately 100%. Further exacerbating the problem, kinetic assays, i.e., assay tests that require rapid repeated measurements, often exceed the speed capabilities of many current readers. As a result of this speed limitation, known readers are poorly suited to combine kinetic assays within the same microplate. In addition, all multi-wavelength microplate readers of which the present inventor is aware are bulky stationary units that take up large amounts of space, for example, on worktops, and are not easily movable between multiple testing locations and are not easily stored out of the way when not in use.

While many microplate readers offer the capability of thermal control of the microplates, existing readers do not offer a suitable means of testing their ability to maintain a consistent temperature across the microplate. This is particularly a problem for microplate tests such as Endotoxin tests, which are used to measure contaminants in injectable drugs, and which are highly sensitive to temperature variations. Innovative Instruments, Inc. (Wake Forest, N.C.) created their Pyro Pak test device to test for temperature control problems common to microplate readers. Their Pyro Pak device tests for temperature inconsistency across a microplate carrier area but their device is limited to an area representing a few wells of a microplate. Further, the Pyro Pak device is not made of the same material as a microplate which results in a different thermal mass which does not have the same thermal properties as a microplate filled partially or completely with samples. Even if a microplate reader is validated with this test device, there still exists no ability to test if the temperature of an actual microplate with test samples is stable and consistent. For example, a microplate of samples placed on a warm or cool countertop may quickly change temperature unevenly across the microplate, causing an unpredictable shift in the optical results, and no existing microplate reader has the capability of measuring or correcting optical errors resulting from this deviation.

SUMMARY OF THE DISCLOSURE

One implementation of the present invention is an optical reader for acquiring optical data corresponding to each of a plurality of sample wells of a cluster of sample wells. The optical reader includes an illuminating array including a plurality of light sources of predetermined differing-wavelength outputs; a detector operatively configured and located to detect light from the predetermined differing-wavelength outputs from the illuminating array; a reading region located between the illuminating array and the detector during operation of the optical reader; and a controller operatively configured to control movement of one, the other, or both, of the illuminating array and the cluster of sample wells and to control pulsing of the plurality of light sources so as to illuminate simultaneously corresponding respective ones of the plurality of sample wells with the predetermined differing-wavelength outputs.

Another implementation of the present invention is a method of acquiring optical data corresponding to each of a plurality of sample wells of a cluster of sample wells. The method includes positioning the cluster of sample wells in a reading region located between a light-source array and a light detector during reading, the light-source array including at least two light sources having differing output wavelengths and located relative to one another so that when the cluster is in a reading position within the reading region, the at least two light sources are located proximate corresponding respective ones of the plurality of sample wells; when the at least two light sources are located adjacent corresponding respective ones of the plurality of sample wells, simultaneously pulsing the at least two light sources so as to direct light toward a first side of the cluster; in coordination with the simultaneous pulsing, sensing via the detector, from a second side of the cluster opposite the first side, light from the at least two light sources that passed through the corresponding respective ones of the plurality of wells; and acquiring optical data corresponding to the light detected by the detector.

Still another implementation of the present invention is an optical reader for acquiring optical data corresponding to each of a plurality of sample wells of a cluster of sample wells. The optical reader includes at least one light source for illuminating at least one of the plurality of sample wells during a reading operation; a detector operatively configured and located to detect light from the at least one light source; a reading region located between the at least one light source and the detector during operation of the optical reader; and at least one non-contact temperature sensor for sensing, during operation, temperature of the cluster at a plurality of locations within the cluster.

Yet another implementation of the present invention is a method of acquiring and processing optical data. The method includes acquiring optical data regarding a plurality of samples located in a corresponding plurality of sample wells of a cluster of sample wells; acquiring, substantially simultaneously with the acquiring of the optical data, temperature data for the cluster; and automatically taking an action as a function of the temperature data.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 17 contains schematic plan views (17A, 17B) of two microplate/array actuating mechanisms and light-source arrays that could be used in an optical reader made in accordance with the present invention.

DETAILED DESCRIPTION

Figure 1:
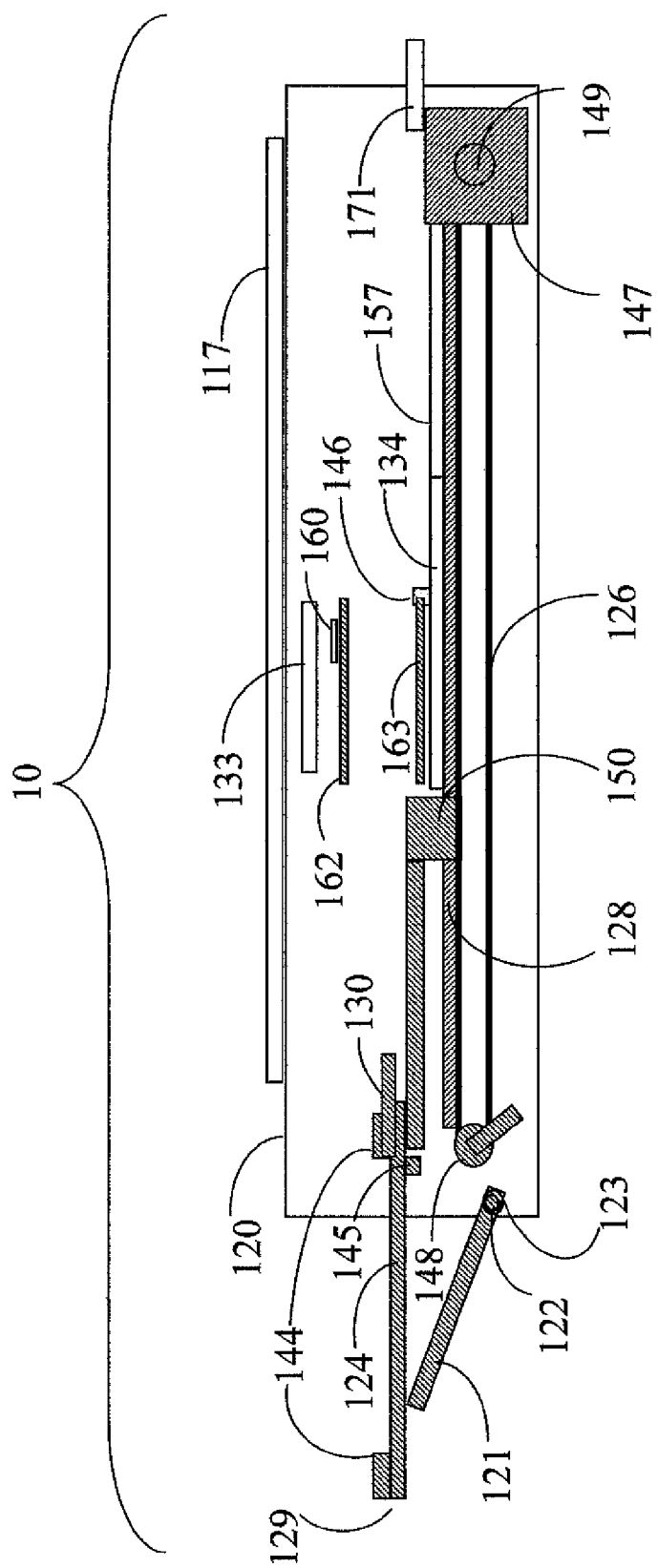
FIG. 1 is a longitudinal schematic elevation view of an exemplary optical reader made in accordance with the present invention.

As mentioned in the Background section above, conventional multi-wavelength microplate readers are bulky instruments that not only take up large amounts of space, but also typically take a relatively long time to acquire assay data taken at multiple differing wavelengths of source light. However, the present inventor has discovered how to read a large number of the wells of a microplate at once, which allows for reading each well with several colors, or wavelengths, of light during a single operation multiple orders of magnitude more quickly than existing methods.

The timing benefit of embodiments of the present invention can be illustrated mathematically, where "t" represents the time, in units of seconds, required to read the plate at a single wavelength. For a conventional microplate reader for an 8×12 sample well cluster (e.g., a 96 well microplate): the read time in seconds for one wavelength=t seconds, for two wavelengths=2 t seconds (i.e., 100% greater than time t for a single wavelength) and for three wavelengths=3 t seconds (i.e., 200% greater than time t for a single wavelength). In sharp contrast, some embodiments of a microplate reader (or more generally, optical reader) made in accordance with the present invention demonstrate the following performance for an 8×12 sample well cluster: read time in seconds for one wavelength=t seconds, for two wavelengths=1⅛ t seconds (i.e., only 12.5% greater than time t for a single wavelength) and for three wavelengths=1¼ t seconds (i.e., only 25% greater than time t for a single wavelength). As can be seen in this example, assuming the time t is the same for both the conventional microplate reader and an optical reader of the present invention, the inventive optical reader of this example is nearly three times quicker than the conventional reader when reading multi-wavelength assays. Using an optical reader made in accordance with the present invention, scientists can combine multiple assays with only a slight fractional increase in total reading time, creating new opportunities in research and clinical diagnostics. When used in a kinetic or high throughput screening application, this difference in performance is significant, allowing the scientist nearly three times or better daily workload throughput in batch microplate processing.

The present inventor has also discovered that this multi-wavelength operating scheme can be implemented in a uniquely small and inexpensive apparatus having a size only slightly taller and wider than the cluster of sample wells, for example on a microplate, being measured and only about four times its length to accommodate movement of the cluster. By using a removable array of multiple wavelengths of monochromatic light emitting diodes (LEDs) as light sources, the present inventor found that cool, long life light sources can be provided that are low in cost, required little or no filtering, are consistent with a very small footprint, and can easily be changed to provide the optical reader with different functionality. Because LEDs are not prone to consumption, i.e. failure, as are halogen lamps in conventional readers, an optical reader made in accordance with the present invention is maintenance-free in comparison.

Because of its small size and mechanical simplicity, embodiments of an optical reader made in accordance with the present invention can be stored on its side, vertically, to conserve bench space in the laboratory. Another benefit of the compact design is that an optical reader of the present invention may be easily placed inside a biological safety hood or be incorporated in compact microplate automation platform such as the SSI Robotics Flash-6X microplate automation station from SSI Robotics (Shoreview, Minn.). Such platforms load microplates into a reader in an automated "high-throughput" application.

In addition, embodiment of an optical reader made in accordance with the present invention may optionally incorporate a new technique for measuring the temperature of the sample wells and the sample wells' contents, thereby enabling new methods of monitoring and adjusting cluster temperature, new methods of identifying temperature variations among the samples, which lead to poor results, and a means of correcting the optical readings to account for variations in the optical results due to temperature variations across the cluster of sample wells.

Referring now to the drawings, FIG. 1 illustrates an optical reader 10 made in accordance with the present invention. In this particular example, optical reader 10 is an absorbance-type reader for collecting light-absorbance optical data from sample wells of a cluster of sample wells, such as is present on a conventional microplate 25 (FIG. 6, FIG. 9), which is illustrated herein for convenience. Although optical reader 10 is an absorbance type reader, those skilled in the art will appreciate that concepts of the present invention may be incorporated into other types of optical readers, including fluorescence-type readers and multimode readers.

As described below in detail, optical reader 10 is configured and programmed to provide, among other things, the unique features mentioned above, such as the rapid multi-wavelength assay and the compact, economical design. While exemplary optical reader 10 is shown as having these feature, those skilled in the art will readily appreciate that other embodiments may have fewer than these features in various combinations. In addition, it will also be appreciated that optical reader 10 is merely a specific example having a particular configuration convenient for explaining various concepts of the present invention. Other examples can have other configurations that differ from the configuration shown. While changes to the configuration shown are not exhaustively addressed for reasons of practicality, some potentially desirable changes are suggested below. Of course, the changes mentioned are not to be taken as exhaustive, but merely illustrative.

Figure 2:
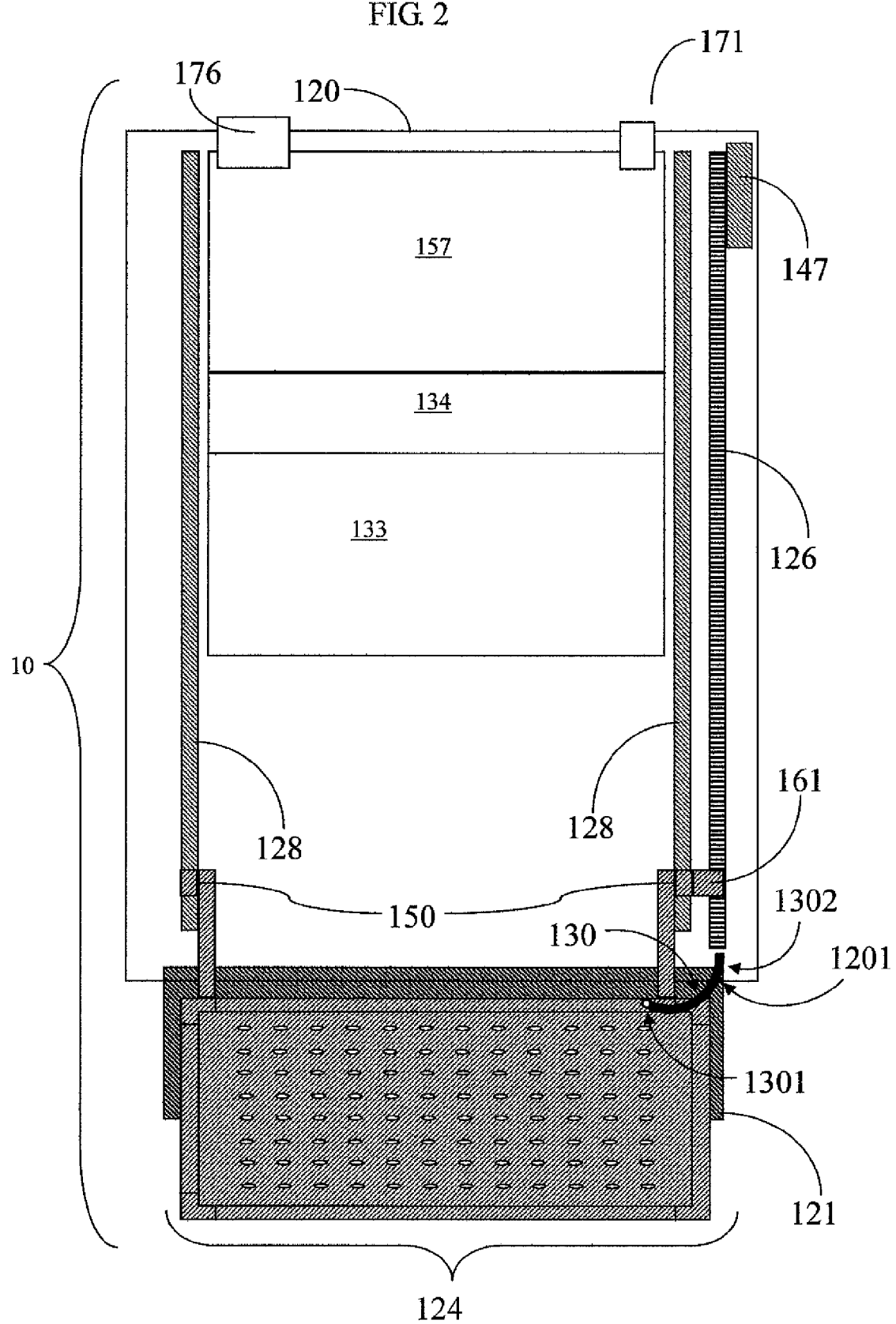
FIG. 2 is a schematic plan view of the optical reader of FIG. 1 with the top cover, keypad and display removed to show interior components.
Figure 9:
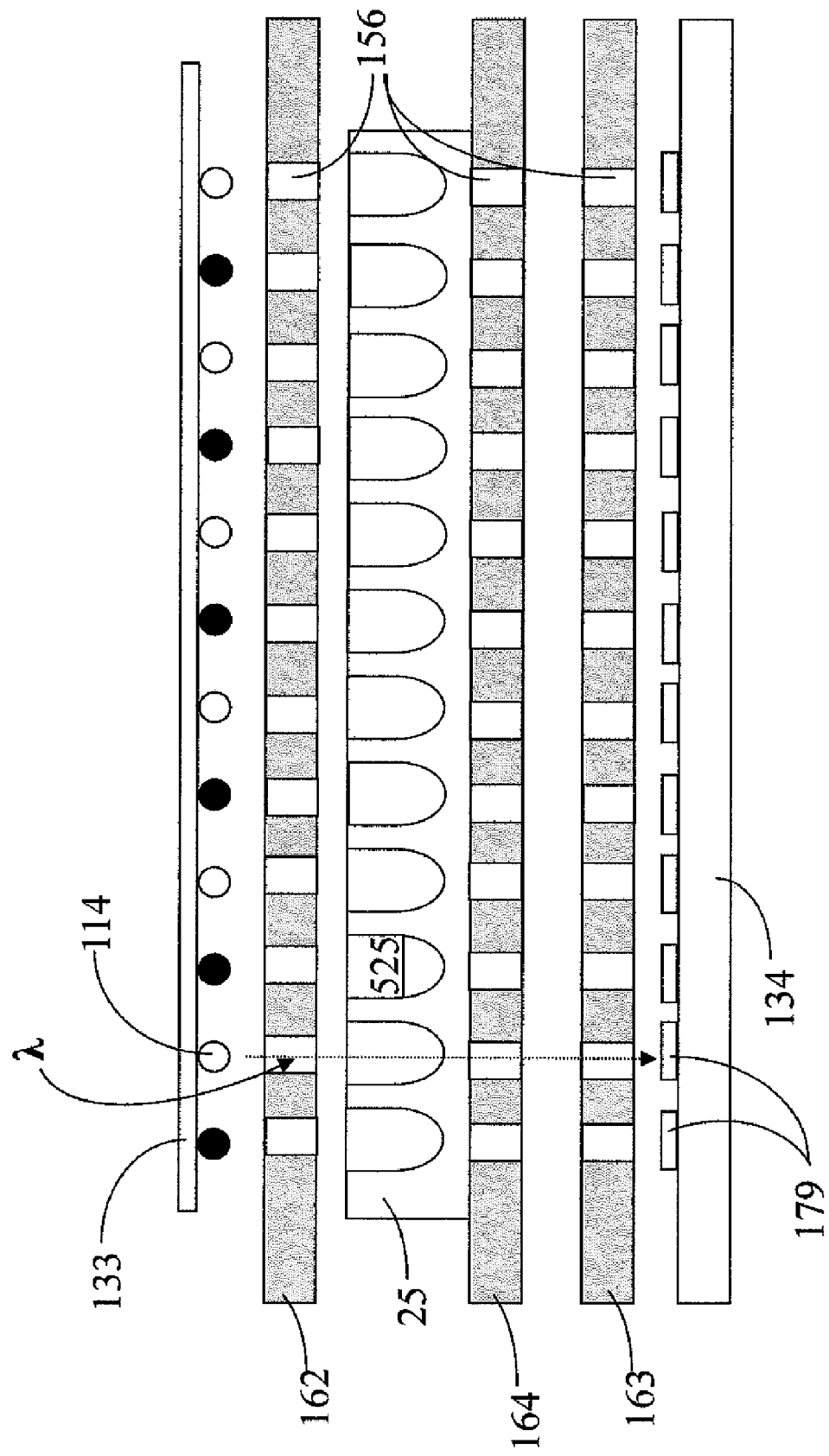
FIG. 9 is an enlarged longitudinal schematic partial elevation view of the optical reader of FIGS. 1 and 2 showing the relation of the LED and detector arrays, the microplate, and collimating masks.

At a high level, optical reader 10 comprises mechanical components, optical components and electronics, as depicted in FIGS. 1 and 2. The optical components include an array of monochromatic light sources, in this embodiment LED array 133, a light detector, in this embodiment photodiode array 134, a plurality of light collimating masks 162, 163, 164 (as also shown in FIG. 9), and a filter 160. It will be appreciated that light collimating masks 162, 163, 164 and filter 160 need not be provided depending on various factors, such as the design of the LEDs 114 in LED array 133 and the nature of the light emitted by these LEDs. LED 114 refers to any of the LEDs in LED array 133 (FIG. 6, FIG. 7) while different wavelength LEDs are denoted by the reference $\lambda_n$, where n is an integer representing the nth wavelength in a series of discrete wavelengths.

As those skilled in the art will appreciate, LEDs are efficient solid state devices that output light in a narrow wavelength range using very little electrical power and generating very little heat. LEDs are available in various wavelengths, focal pattern, size and power from several industrial sources such as Digi-Key Corporation (Thief River Falls, Minn.). Depending on their character, LEDs may require little or no additional optical filtering when used in the described apparatus. They may have built-in lenses so that no additional focusing may be needed. Their low cost allows a plurality of individual LED light sources of different wavelengths to be positioned in one or more rows of the array to allow each well of the microplate to be measured at a plurality of wavelengths. Other embodiments may use a different type of monochromatic light source, such as one or more Organic Light-Emitting Diodes (OLED) (One Stop Displays, Winter Park, Fla.), lasers (Coherent, Inc., Santa Clara, Calif.) or laser diodes (Photodigm, Inc., Richardson, Tex.), and yet other embodiments may use a combination of different types of monochromatic light sources.

Figure 6:
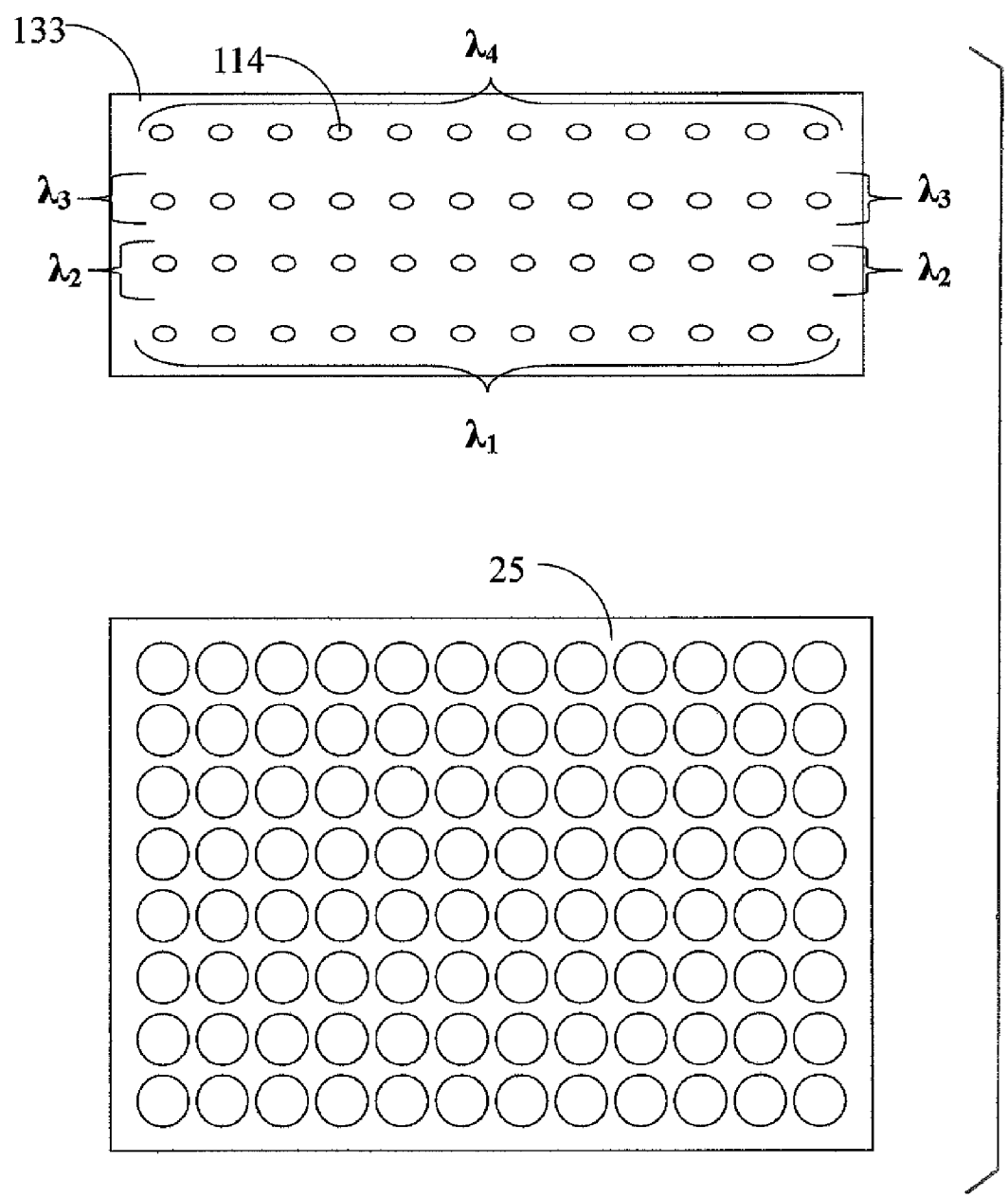
FIG. 6 is a view of the LED array of FIGS. 1 and 2 shown beside a microplate for perspective.

As shown in FIG. 1, LED array 133 may be a rigid card of printed circuit board material. As shown in FIG. 6, LED Array 133 may include a one or two dimensional multi-wavelength array of LEDs 114, such as a twelve-by-four (12×4) LED array 133 arranged with 9.0 mm on-center spacing for use with a 96-well microplate 25. LED array 133 may include four rows of twelve each LEDs, each row containing twelve LEDs of the same wavelength with each row having different wavelengths from the other rows. In other embodiments, LED array 133 could be arranged in a 1-by-4 array (as illustrated by LED array 1633 of FIG. 16) or 2-by-2 LED array (as illustrated by LED array 1733A and 1733B of FIG. 17 of one each of four different wavelength LEDs, or 8-by-4 array of eight each of 4 different wavelength LEDs. In these embodiments, the "4" dimension of the array defines four available wavelengths (represented as $\lambda_1, \lambda_2, \lambda_3, \lambda_4$) but other embodiments may have more or fewer wavelengths. In various embodiments, LEDs 114 may be spaced at distances other than 9 mm, for example, 4.5 mm, 18 mm (FIG. 17), 27 mm, or other distances or combinations thereof.

Figure 16:
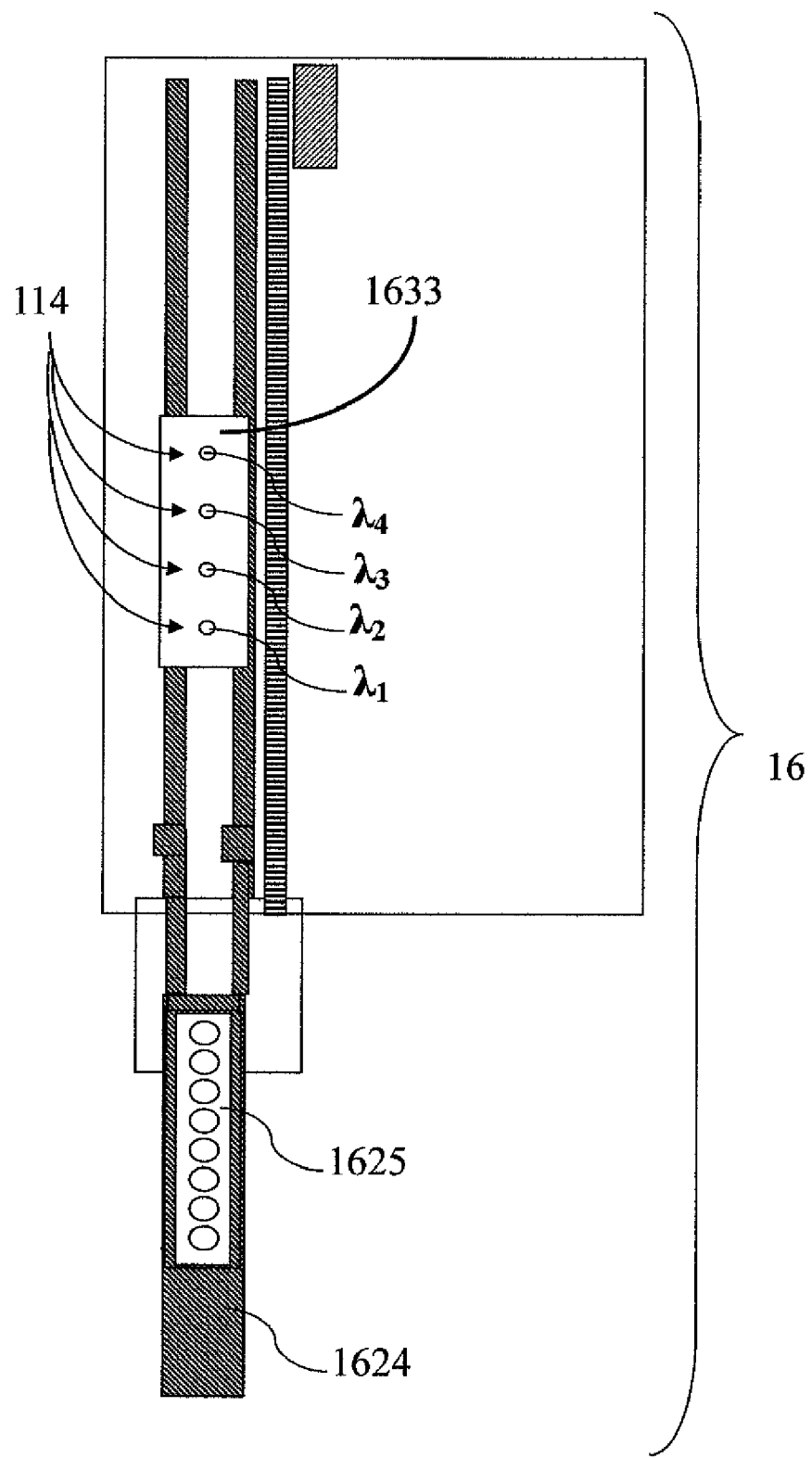
FIG. 16 is a schematic plan view of yet another optical reader made in accordance with the present invention that is particularly adapted for reading a one dimensional array of clustered sample wells.

Other embodiments may arrange the arrays to read differently designed microplates such as a 384-well microplate or a 60-well, 72-well, or 96-well Terasaki® microplate from manufacturers such as One Lambda Inc. (Canoga Park, Calif.). Some brands and models of microplates contain removable wells that can be separated from the adjacent wells individually or as strips of wells. An alternative optical reader 16, shown in FIG. 16, is configured to read these individual wells or individual strips of wells separate from a microplate or microplate frame. Other embodiments may include an asymmetric array of light sources, as shown, for example, in light-source array 733 of FIG. 7.

Figure 7:
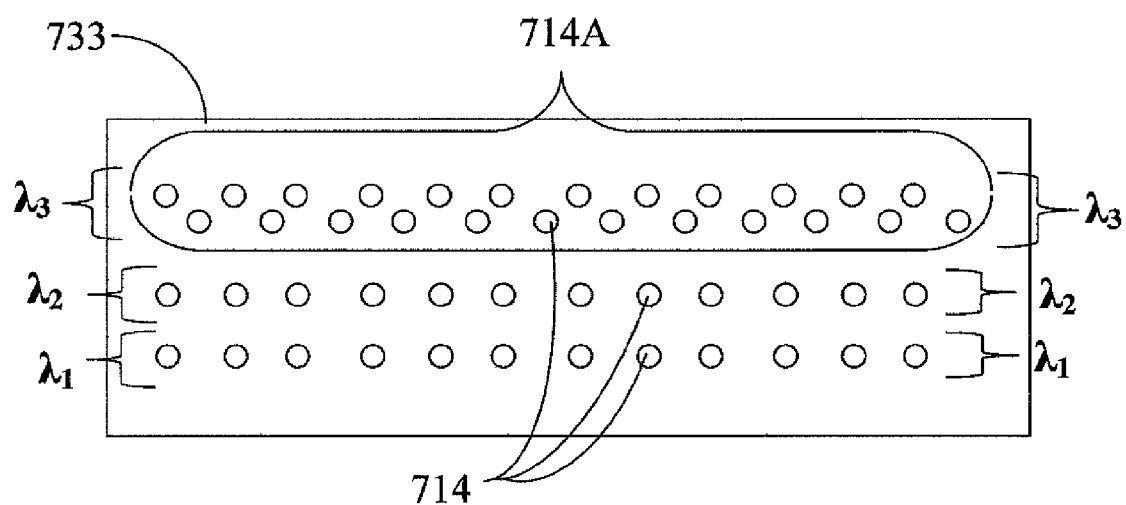
FIG. 7 is a view of an alternative LED array that could be used, for example, in place of the LED array of FIGS. 1, 2 and 6.

Referring to FIG. 7, light-source array 733 includes light sources 714 arranged in a pattern other than rectangular, in this example a zigzag pattern in sub-array 714A. Other embodiments may arrange the array so that same-wavelength LEDs are not directly adjacent to one another when more than one LED of each color is present in the array. Referring again to FIG. 1, LED Array 133 may be removed from optical reader 10 and replaced by an LED array with different wavelength LEDs or differently spaced LEDs to provide different functionality. Depending on the type of detector used, differently spaced LEDs would be matched with a similarly spaced detector array.

LEDs can vary in spectral output (wavelength) based on their temperature, which can be manipulated by altering the electrical current or voltage across the LED. Using this characteristic, an LED may be manipulated to output light at different controlled wavelengths based on the voltage, current, or duration thereof applied to the LED. While LEDs are available in many of the wavelengths used in the art of microplate reading, alternative wavelengths may be measured by using broader spectrum LEDs and a filter 160 of optical filtering material. In this case, it is the combination of the LED and corresponding filter(s) that work in cooperation to provide a particular wavelength light source. Filter 160 may be constructed from scientific optical filter material as is available from companies such as Chroma Technology Corp. (Rockingham, Vt.) and Omega Optical, Inc (Brattleboro, Vt.). Filter 160 may be placed across one or more LEDs, one or more rows of LEDs or across one or more rows of corresponding photodiodes or in combinations of the two. The additional filtering would have the same effect as wavelength specific LED light by limiting the broader spectrum LED light to a wavelength of interest before the light reaches the photodiode light detection surface. Filter 160 may be flat or lens shaped or it may be flat and used in conjunction with a lens.

Alternatively, filtering is available in the form of wavelength specific photodiodes, such as Hamamatsu Photonics K.K. (Bridgewater, N.J.) S2684 monochromatic series of photodiode components. For measurement purposes, and from a scientific perspective, whether the filtering of light takes place before the sample at the LED, or after the sample at the photodiode, is irrelevant. Either method yields an equivalent result. The optical reader 10 may use a combination of these methods to measure various wavelengths. In yet other embodiments, filtering may be provided by directing LED light into a monochromator or prism, or prismatic device, to split a broader wavelength output into a narrower bandwidth wavelength of interest.

Figure 8:
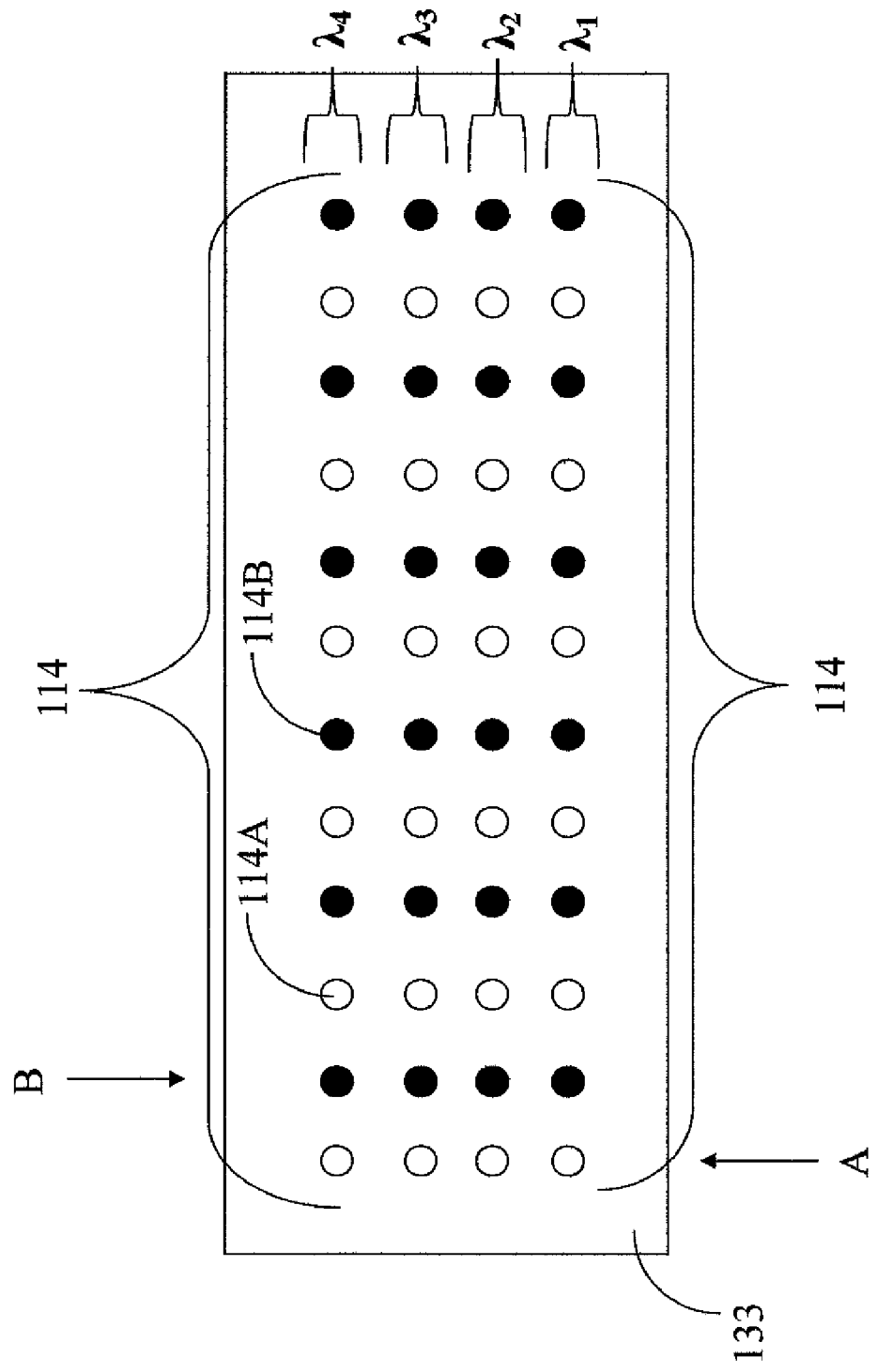
FIG. 8 is a diagram illustrating the illumination sequence of the LEDs within the LED array of FIGS. 1, 2 and 6, with the dark-colored LEDs being idle (non-powered) LEDs and the light-colored LEDs representing illuminated LEDs.

FIG. 8 depicts a particular illumination scheme in the context of optical reader 10 of FIGS. 1 and 2. As shown in FIG. 8, each of the twelve LEDs 114 in the first row of LED array 133 provides light at one wavelength, for example, a wavelength of 405 nanometers (nm) (identified as "$\lambda_1$"). Each LED $\lambda_2$ in the second row of twelve LEDs provides light at a second wavelength, for example 450 nm (identified as $\lambda_2$). LEDs 114 in the third and fourth rows provide light, respectively, at third and fourth wavelengths, for example 490 nm (identified as $\lambda_3$) and 625 nm (identified as $\lambda_4$). Thus, up to 48 wells of microplate 25 can receive light of four different wavelengths at one time. Repeatedly moving carrier 24 one well distance (9 mm for a 96-well plate) between readings allows all the wells of microplate 25 to be quickly read at multiple wavelengths in a single operation.

In various examples, the LEDs, such as LEDs 114, may be illuminated or pulsed all at once or they may be pulsed in a sequence relative to one another. In one particular example, the LEDs may be illuminated in alternating columns to minimize light intended for one microplate well from reaching an adjacent well's detector. In the example of FIG. 8, the odd columns of microplate 25 may be illuminated as the microplate passes into optical reader 10 (arrow "A"), and then the even columns of the microplate may be illuminated as the plate reverses direction and passes back out of reader (arrow "B"). The scientist experiences no loss in reading time as the plate would have to come back through the optics whether or not the even column LEDs were used from the forward or reverse pass. In this example the odd ones of LEDs 114 for each wavelength (i.e., the ones of the LEDs in positions 1, 3, 5 . . . 11) may be powered 114A as microplate 25 passes into optical reader 10, and the even ones of the LEDs 114B (i.e., the ones of the LEDs in positions 2, 4, 6 . . . 12) may be powered as microplate 25 moves out of optical reader 10.

Figure 10:
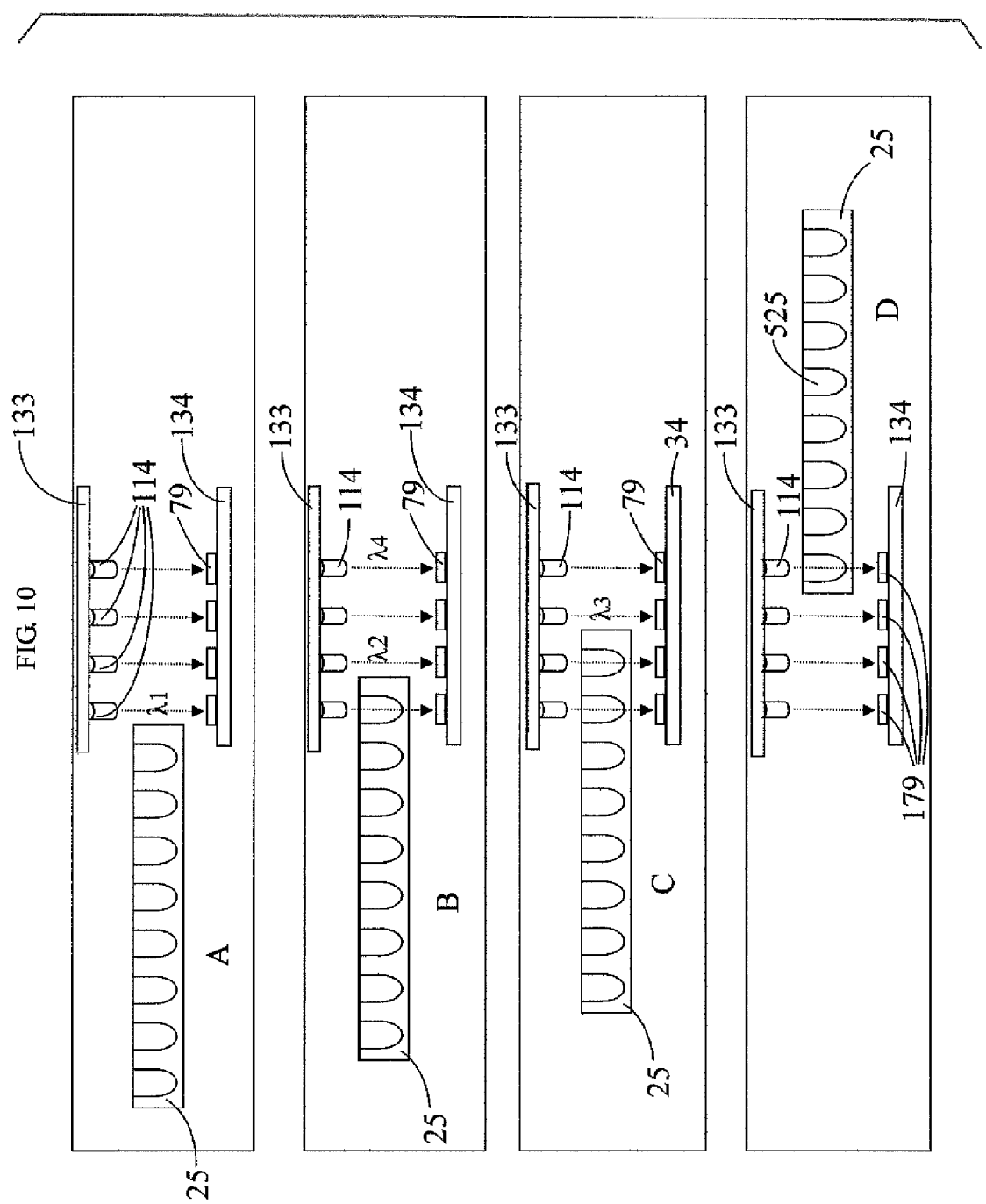
FIG. 10 is a series of longitudinal schematic elevation views (A-D) showing an exemplary microplate movement and illumination method that can be implemented in, for example, the optical reader of FIGS. 1 and 2.

A microplate flow chart is provided in FIG. 10 showing the plate reading process for microplate reader 10. In response to a user command through the display keypad 117 or via USB port 171, at stage A, the reader measures full light values and dark reader (no light) background values, converts them to digital data and writes the net result to memory as $T_{max}$, or 100% (light) Transmission. As the $1^{st}$ row of sample wells of microplate 25 slide into the light path, the motor 147 stops just briefly to measure the reduce transmittance of light $\lambda 1$ due to the light absorption by microplate 25 and samples therein, and writes them to memory, Step B. The microplate 25 moves so the next row (and then measures and record readings for both rows one and two at the two available wavelengths ($\lambda 1, \lambda 2$), Step C. The process continue until all the wells are read at all the desired wavelengths, then turns back to sent the plate out (Step D) and in some embodiments, reads the even column subset of well (not shown). In the PLD circuits 1101, relative percent light transmitted is converted into a unitless measure of absorbance, defined by Beers Law as Absorbance=$Log_{10}(T\%)$ where T % is the net relative transmission of light through the sample wells 525.

Figure 11:
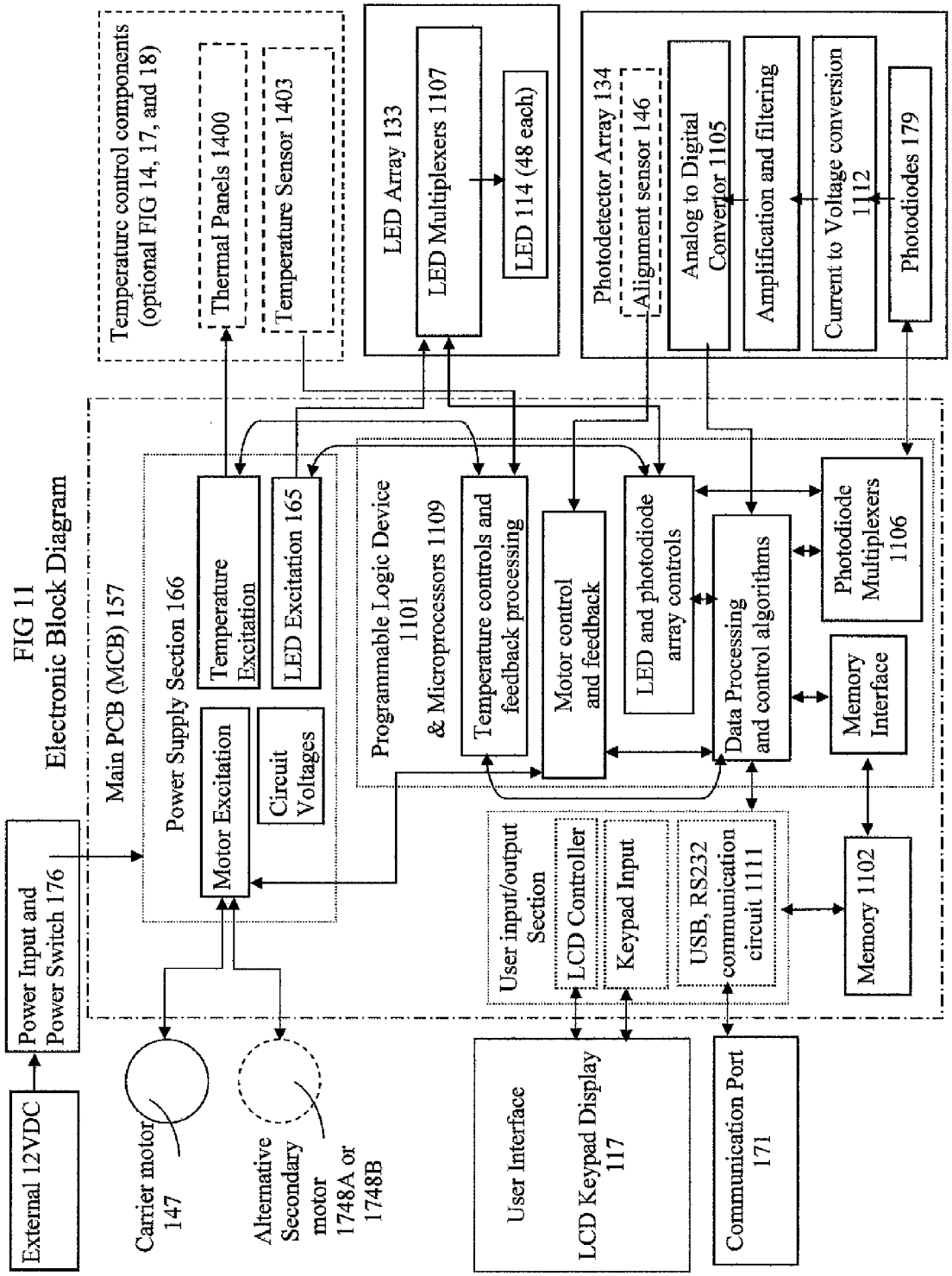
FIG. 11 is an block diagram illustrating the connectivity of electronic components of the exemplary optical reader of FIGS. 1 and 2.
Figure 12:
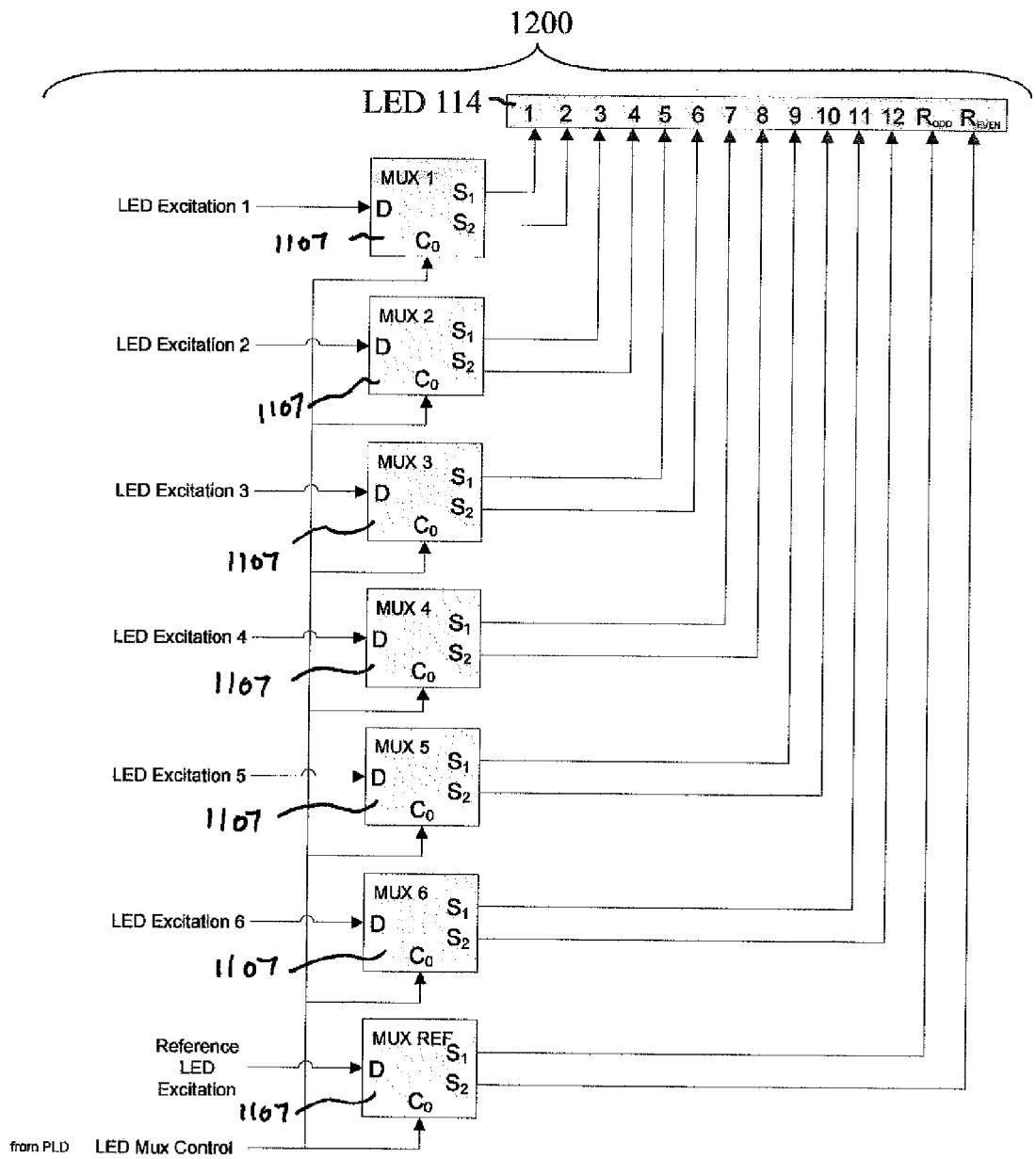
FIG. 12 is a schematic diagram of exemplary illumination electronics for the LED array of FIGS. 1, 2 and 6.

Circuitry 1200 to control this illumination process is illustrated in the schematic, FIG. 12 and FIG. 11. In FIG. 12, circuitry 1200 illustrates the multiplexer (MUX) arrangement and connections for the $1^{st}$ row ($\lambda 1$) of LED 114, which would be duplicated for Rows $\lambda 2, \lambda 3$, and $\lambda 4$. For clarity, additional duplicate row circuits are not shown. The first LED of $\lambda 1$ is abbreviated "1", and so one. This schematic includes and example or how reference LEDs, denoted "Rodd" and "Reven" would be wired as well if the circuit is applied to an embodiment utilizing reference LEDs as described below.

In other embodiments of an optical reader made in accordance with the present invention, a mechanical shutter (not shown) with holes cut out for a subset of LEDs may be used and may be activated by a shutter solenoid (not shown). Various embodiments of shutters may be used to controllably mask a subset of the LEDs to prevent adjacently illuminated LEDs from interfering with unintended photodiodes. Shutters, masks and solenoids of this type are available from, for example, Brandstrom Instruments, Inc. (Ridgefield, Conn.) or may be mechanically or laser cut from opaque material such as sheet metal. Movement of a shutter may be monitored by a main circuit board (MCB) 157 using an optical sensor, such as the model number QVE11233 from Fairchild Semiconductor (South Portland, Me.). Alternatively, a solenoid may include a self-contained sensor to track the position of solenoid and shutter.

In other embodiments, rather than using a shutter to shield a subset of LEDs, the LED array may have a set of LEDs for every other column of the plate. The entire LED card may be moved by a solenoid or stepper motor. In such embodiments, all the LEDs may be illuminated at once but only every other column of the microplate is illuminated depending on the position of the LED array.

Further embodiments may utilize reference LEDs and reference photodiode pairs to further reduce variability in the measurements. The LED array may include one or more reference LEDs for each wavelength, each paired with a corresponding reference photodiode. Photodiode readings from the reference LEDs are used to adjust for LED stability in all light measurements. For example, as the light intensity of the reference LED increases due to a drift in voltage to the LED, the light intensity of the corresponding measurement LEDs increases by the same factor. The net change in output can be factored out of the sample measurement mathematically. This mathematical adjustment would take place in the programmable logic device (PLD) or microprocessors of MCB 157.

As illustrated in the block diagram of FIG. 11, the excitation signals (electrical current) to the LEDs 114 of array 133 may be provided by constant current source LED drivers 165, which may be provided in power supply 166 section of MCB 157. Optical reader 10 of FIGS. 1 and 2 may use, for example, part number LM2796 LED drivers from National Semiconductor (Santa Clara, Calif.), or similar devices. Electrical current is sent from power supply 166 to LED array 133. In an embodiment where the LEDs are not illuminated all at once, the LED excitations may be multiplexed using an electronic multiplexing device such as the part number ADG758—CMOS (Low Voltage, 3Ω 8-Channel Multiplexer) from Analog Devices Inc. (Norwood, Mass.). In one example, optical reader 10 measures light from LEDs 114 by integrating the measured signal of an LED pulse to establish a baseline LED output, and then compare this measurement to the measured integrated pulse with a microplate, such as microplate 25, in the light path. Other embodiments may measure the average of one continuous illumination pulse or several pulses.

Figure 13:
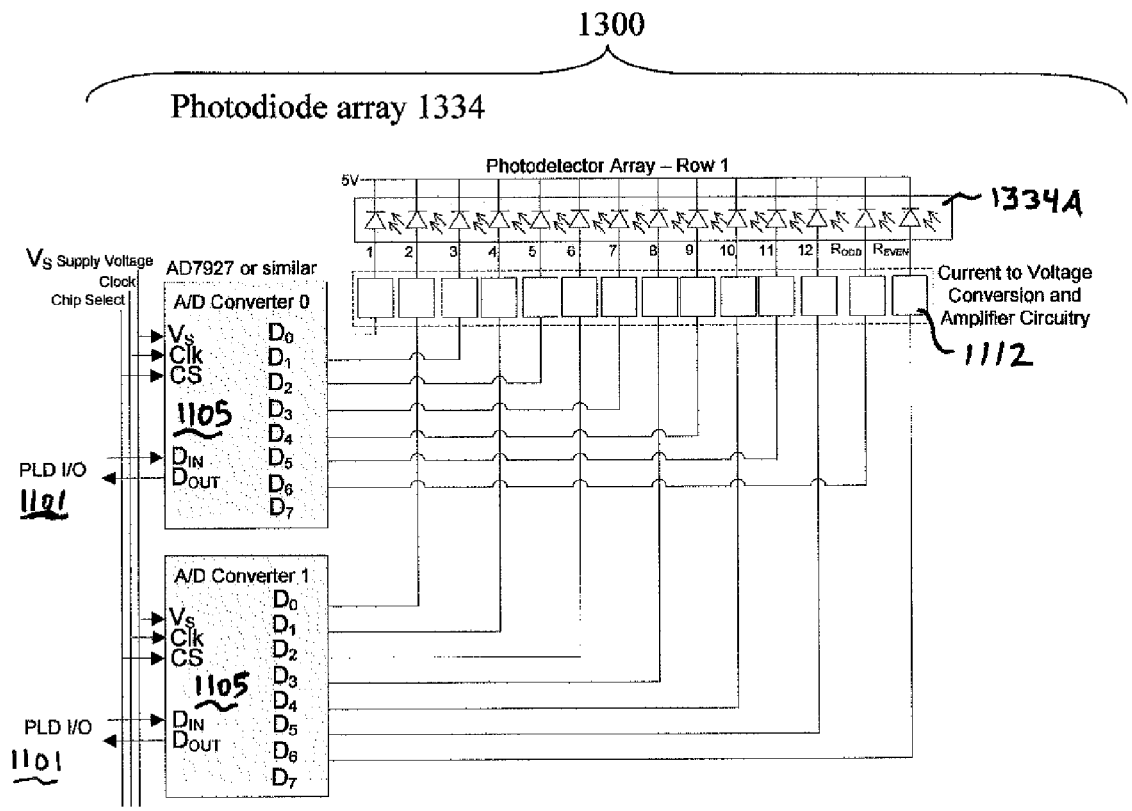
FIG. 13 is a schematic diagram of exemplary data collection electronics for the photodiode array of FIGS. 1, 2 and 6.

FIG. 13 illustrates the schematics for a subset of the photodiode detection circuit. FIG. 13 also provides guidance for integrating a reference channel into circuit 1300. Circuit 1300 shows one row of photodiode detectors using normal schematic conventions, showing the wiring of the photodiodes to the A/D converter then following the signal out of the circuit to the PLD I/O inputs as described in further detail in FIG. 11.

Further detail of exemplary optical reader 10 is shown in FIG. 9, wherein the light λ from LED array 133 is shown as being collimated with an opaque plastic or metal "mask" 162, 163, and 164 containing aperture holes 156. Aperture holes 156 may be oval, round, elliptical, or other shapes. In this example, mask 163 is placed over the photodiode array 134. In other embodiments, different combinations of masks, here, masks 162, 163, 164, may be used to collimate light. In this example, mask 162 adjoins LED array 133, mask 164 is integrated as part of carrier 124 (FIG. 2), and mask 163 adjoins photodiode array 134. Also shown in FIG. 9 is microplate 25 and twelve microplate wells (microwells) 525.

In exemplary optical reader 10 of FIGS. 1 and 2, photodiode array 134 contains a 12×4 array of photodiode s 179 (shown in cross section side view FIG. 5) spaced and placed such that, when microplate 25 is positioned into various reading positions within the reading region between the photodiode array and LED array 133, each photodiode 179 is centered under a corresponding sample well 525 (FIG. 5) of the microplate with a corresponding one of LEDs 114 aligned on the opposite side of the microplate. Masks 162, 163, 164 are not shown. Note that a subset of the sample wells 525 is labeled for clarity in the figure. In addition, an optional temperature sensor 503 is illustrated to shown its relative placement as described in greater detail in embodiments described in FIG. 14, FIG. 15, and FIG. 18. Other geometric embodiments of LED arrays could be matched with a corresponding arrangement of photodiodes so that each LED is aligned with a photodiode for the purpose of light measurement. Hamamatsu Photonics K.K. (Bridgewater, N.J.) is one provider of photodiodes, and both their S2684 monochromatic and S1226/S1227 broad spectrum photodiodes are well suited for this application.

Other embodiments may use a different type of light detector in place of a photodiode or a plurality thereof, such as one or more charge coupled device (CCD) sensors (Sarnoff Imaging Systems, Princeton, N.J.) or one or more photomultiplier tubes (Hamamatsu Photonics K.K., Bridgewater, N.J.) or one or more photodetector ICs (PDIC) (Atmel Corporation, San Jose Calif.).

Alternative embodiments may use an array of photodiodes of unequal number relative to the light sources in the LED array and move either the photodiodes or LEDs relative to one another, reusing the same photodiodes with different LEDs or vice-versa. Yet other embodiments may attach the photodiodes beneath the carrier and move the combined carrier-photodiode component relative to the LED array while sending the photodiode signal to the MCB via a flexible cable. The reverse could be constructed using an LED array attached to the carrier and with filtered or wavelength specific photodiodes above.

As each photodiode 179 is illuminated with LED light (FIGS. 9, 10, and 11), the analog signals from the photodiodes may be multiplexed using electronic multiplexing devices such as ADG758—CMOS Low Voltage, 3Ω 8-Channel Multiplexer from Analog Devices Inc. (Norwood, Mass.), or similar devices, and then converted to a digital signal via Analog-to-Digital conversion (A/D) devices, such as part number AD7927—8-Channel, 12-Bit A/D Converter from Analog Devices Inc. (Norwood, Mass.). The output of the A/D may be sent directly to a microprocessor. Photodiode array 134 may include a microprocessor, memory, motor drivers and other electronic components or the card may be constructed to exist separately with another circuit board, for example, MCB 157, containing said components, as illustrated in FIG. 11.

MCB 157 may be separate from photodiode array 134. On MCB 157, a programmable logic device (PLD) 1101, such as the Spartan series XCS1500L field programmable gate array available from Xilinx Inc. (San Jose, Calif.)) may be used instead of microprocessors or with a smaller subset of microprocessors. MCB 157 may include electrical connections to carrier motor 147 (FIG. 1, FIG. 11), it may contain a relational position sensor 146 for carrier 124 as well as communication port 171 to connect with external devices such as a computer, as illustrated in FIG. 1 and in the block diagram FIG. 11.

PLD 1101 contains all control algorithms for motor 147, LED excitation 165, photodiode array 134, LCD Keypad Display 117, and internal memory 1102. Memory 1102 may be implemented with standard off-the-shelf ICs controlled by PLD 1101, microprocessors 1109 or equivalent. All processing of data from photodiodes 179 may be performed on MCB 157. MCB 157 may include embedded non-volatile memory 1102 for storage of processed data and configuration data, as shown in FIG. 11.

In one embodiment, the voltage signal from each photodiode 179 may be amplified and filtered electronically, and then sent through an analog-to-digital (A/D) converter 1105, such as the part number AD7927—8-channel, 12-Bit A/D converter from Analog Devices (Norwood, Mass.). The electrical outputs of photodiodes 179 may be multiplexed into 7 of the 8 input channels of A/D converter 1105. The digital output of A/D converter 1105 may be sent directly into PLD 1101 and stored in memory 1102 As with LED array 133, the number of signals passed between photodiodes 179 and PLD circuit 1101 or microprocessor 1109 may be minimized by multiplexing the conditioned photodiode outputs with multiplexer device 1106, such as the ADG758—CMOS 8-channel multiplexer from Analog Devices Inc. (Norwood, Mass.) before passing the signals into PLD 1101. PLD 1101 may control multiplexers 1107 such that matching pairs of LEDs 114 and photodiodes 179 are processed simultaneously. Multiplexers 1106 may alternatively be place on the photodiode array 134 and may be configured in the same manner to use the same control signals. The photodiode signals that are not being intentionally or actively measured may be ignored by the software.

The tables in the schematic diagrams illustrated in FIGS. 12 and 13 detail how alternate columns of LEDs 114 may be turned on when the control input signal from microprocessor 1109 changes. These schematic figures also teach how embodiments including reference photodiodes could be constructed although these reference elements represent alternative embodiments and are not shown.

MCB 157 (FIG. 11) may provide means for conditioning the 12 Volt DC (VDC) power input 176 and implementing the keypad 117. MCB 157 may contain PLD 1101 that processes data from the conditioned photodiode signals, controls the activation of LED and photodiode arrays 133 and 134 and controls all other subsystem circuits, including internal memory 1102 and motors 147.

A power supply circuit 166 may accept an external 12 VDC input via a power input port 176. This design can allow the 12 VDC input to be sourced from a variety of devices, such as an AC power adapter with 12 VDC, 14 VDC or 15 VDC output, or another 12 VDC power source, such as a car battery or a portable external 12 VDC battery for use in the field, such as when conducting water-quality or other research in remote areas. Power circuit 166 converts the input voltage into the voltages required for PLD 1101 and passive components, such as memory 1102, Photodiode array 134, multiplexers 1106 and 1107 on both the MCB 157 and LED array 133. The input voltage would also be converted into motor excitation and LED array excitation signals in the power supply section 166.

Small openings (not shown) may also be provided through enclosure 120 of optical reader 10 for data communication port 171, a combination power (on/off) switch and power input 176 and for the described in block diagram FIG. 11. MCB 157 may provide the control signals to the keypad display 117. User menu options presented on the display may include carrier 124 agitation, optical measurements, duration, frequency and amplitude of agitation, temperature control, internal diagnostic tests, and sending data out of optical reader 10 through communication port 171.

The communication port circuit 1111 may include standard hardware driver devices (not shown) for universal serial bus (USB) communication protocols. Optical reader 10 may have the ability to communicate with an external PC with a USB cable connection or embodiments may include RS232 standard, infrared, or wireless USB communication or combinations of these formats and methods. The communication port circuitry 1111 and communication may be controlled by PLD 1101 using software algorithms. The communication port 171 may also export data and may output a data file, such as an electronic file complying with American standard code for information interchange (ASCII) standards, to a plug-in USB memory device such as a SanDisk Cruzer® Micro USB Storage device (SDCZ4-256-A10) from SanDisk Inc. (Milpitas, Calif.). In this way, the user may easily shuttle data from optical reader 10 to a PC for further analysis without connecting the PC to optical reader 10 by a cable.

Enclosure 120 may be constructed of sheet metal (aluminum or steel), but can be constructed of other opaque materials such as a metal casting or plastic, such as molded plastic. A metal enclosure has the additional benefit of providing electrical shielding to the electronics so that other devices that emit electrical interference will not affect optical reader 10 electronics within enclosure 120. Non-metallic enclosure material may be coated with a conductive paint or covered in a conductive foil to provide similar protection from electrical interference to a metal enclosure. Alternatively, within enclosure 120, the electronic circuits could be surrounded by a conductive sub-enclosure for purposes of electrical shielding.

Adhered to the top surface of enclosure 120 may be a liquid crystal display (LCD) touch screen keypad display 117, such as part number MK-AOG from Amulet Technologies, (Santa Clara, Calif.) that combines the keypad and a visual user interface. Alternatively, Display F-5143NFU-FW-AA from Optrex America, Inc., (Plymouth, Mich.) could serve as a display along side a membrane keypad as available from Nelson Switch Plate (Los Angeles, Calif.) or Pannam Imaging (Cleveland, Ohio) could be attached to provide a user interface. Other types of displays, such as LED or plasma, could be used. The display may permit scrolling so a user can see the optical data on the display. The display may also offer user options, such as the commands to read microplates at various wavelengths, with the options for microplate shaking and temperature control. Other choices may include running internal diagnostics tests or exporting the data to a memory device or external computer. Other embodiments may include another type of graphic or text display, or a touch-screen display, such as an OLED display that could function as both display and keypad. Further embodiments intended for control remotely through an external computer may include a keypad only or neither keypad nor a display, with all user interaction controlled via a communication port, which may be similar to port 171 of optical reader 10, connected computer or via wireless control or by an infra-red or other external communication means.

Optical reader 10 as shown in FIG. 1 may include a door 121 constructed of a plastic or metal material that is hinged along the bottom edge and spring-loaded via spring 123 to stay closed when carrier 124 is inside the optical reader. Door 121 may be pushed open by a leading edge 129 of carrier 124. Microplate 25 (not shown) can then be placed onto carrier 124 by a user. Door 121 closes by the force of spring 123 as carrier 124 retracts into the enclosure 120. Enclosure 120, door 121, and carrier 124 material may be opaque and non-reflective so that light from outside optical reader 10 does not penetrate the device during light measurement and so that unfocused light from LED array 133 is not reflected inside the optical reader.

Figure 14:
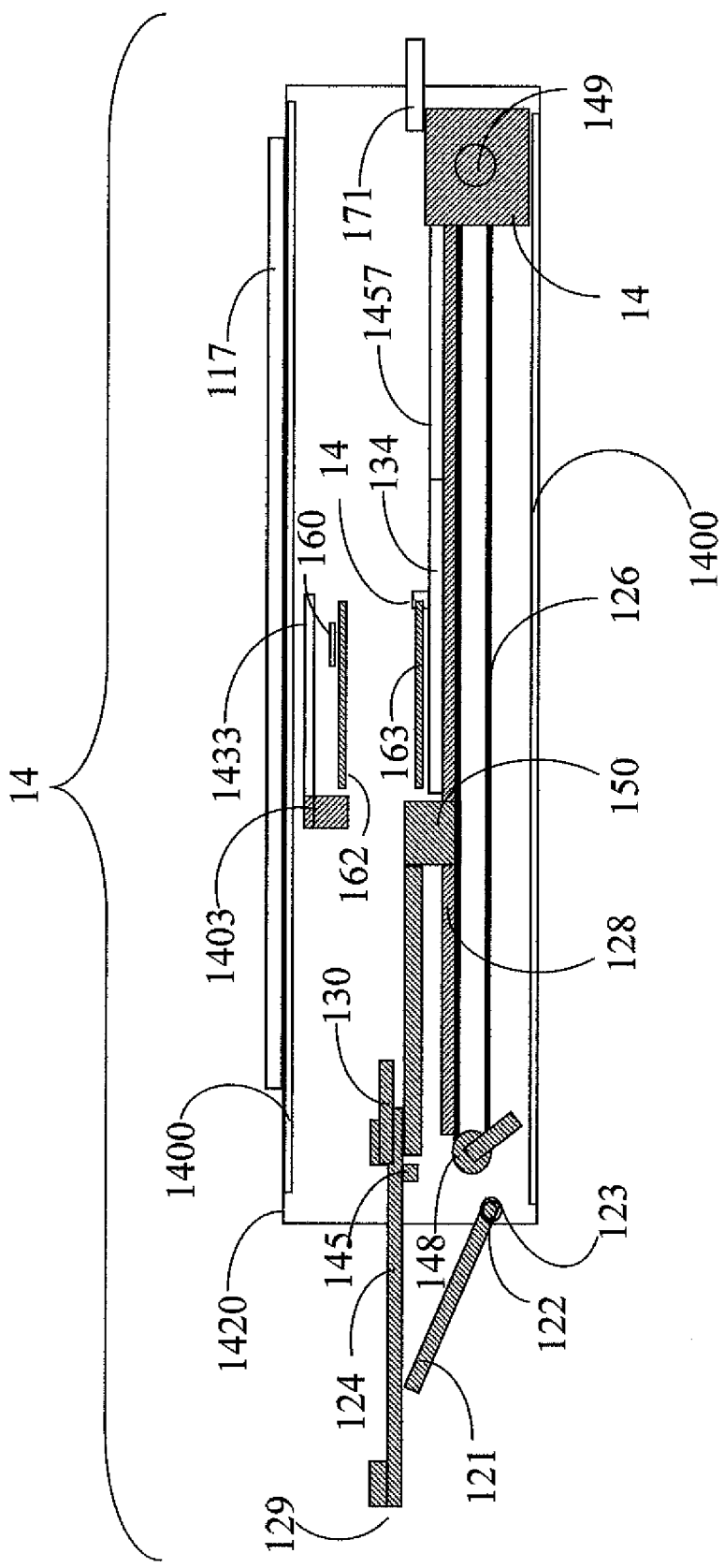
FIG. 14 is a longitudinal schematic elevation view of another optical reader made in accordance with the present invention that includes temperature control and temperature monitoring components for temperature control and optical data correction.

Alternative embodiments of an optical reader made in accordance with the present invention may include the ability to control the temperature inside. FIG. 14 illustrates an optical reader 14 that includes such temperature control. It is noted that components of optical reader 14 shown but not described, may in some examples be the same as the corresponding components of optical reader of FIGS. 1 and 2. Other components referenced the same as similar components in FIG. 1 and in fact the same as described in FIG. 1, for example door 121. Other changes may be made as well. For example, the reading operation need not include simultaneous pulsing of multiple differing color light sources. Rather, in this respect, optical reader 14 of FIG. 14 may operate in a conventional manner. Optical reader 14 may control temperature internally via electronically controlled thermal panels 1400, such as part number HK5467 (Minco, Minneapolis Minn.). Panels 1400 are typically self-adhesive and may be adhered to the inside surface of enclosure 1420 to warm or cool the interior of optical reader 14 and the samples and microplate (not shown) (or alternative sample vessel or cluster of sample wells, such as a group of test tubes held, for example, in a suitable rack). Panels 1400 may be alternatively attached mechanically using screws, rivets, clips or some other mechanical means.

Figure 5:
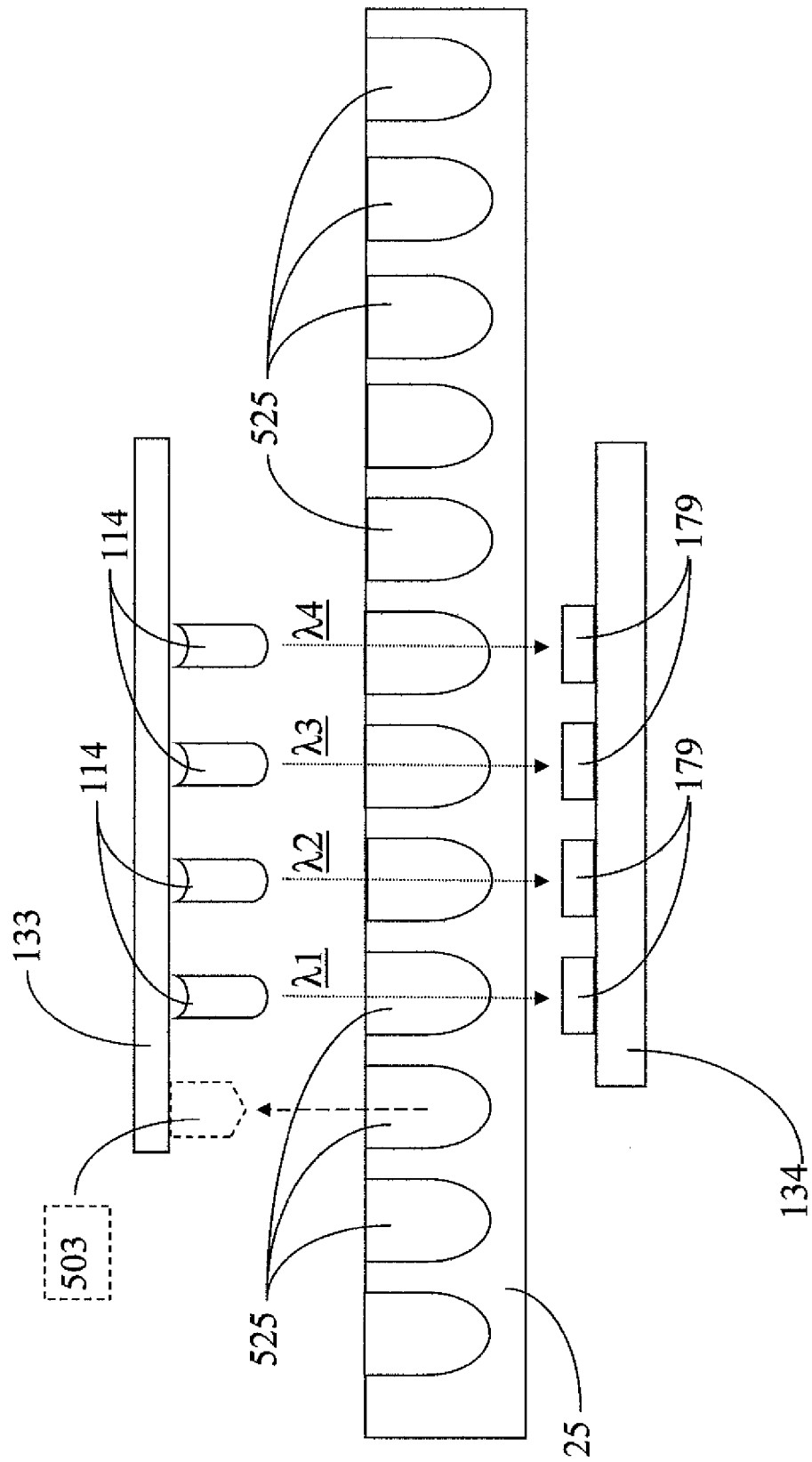
FIG. 5 is an enlarged schematic elevation view of the LED and detector arrays of the optical reader of FIGS. 1 and 2.

In embodiments with one or more sensors, such as sensors 1403, (or 503 in FIG. 5) integrated into LED Array 1433 (or 133 in FIG. 5), each sensor may be aligned in the same spatial array arrangement as the LEDs, that is, 9.0 mm on-center relative to the other components, or it could be mounted in a combination or plurality of these locations. In these embodiments, temperature readings of a well can be recorded while optical readings of adjacent wells are recorded. By using non-contact optical temperature sensor 1403, MCB 1457 may monitor the temperature and adjust the temperature of heating panels 1400 by adjusting the current or voltage provided thereto. This allows the user to adjust the temperature based on direct temperature measurements of microplate 25 (as shown in FIG. 5) sample vessel 525 and/or the contents thereof.

Figure 18:
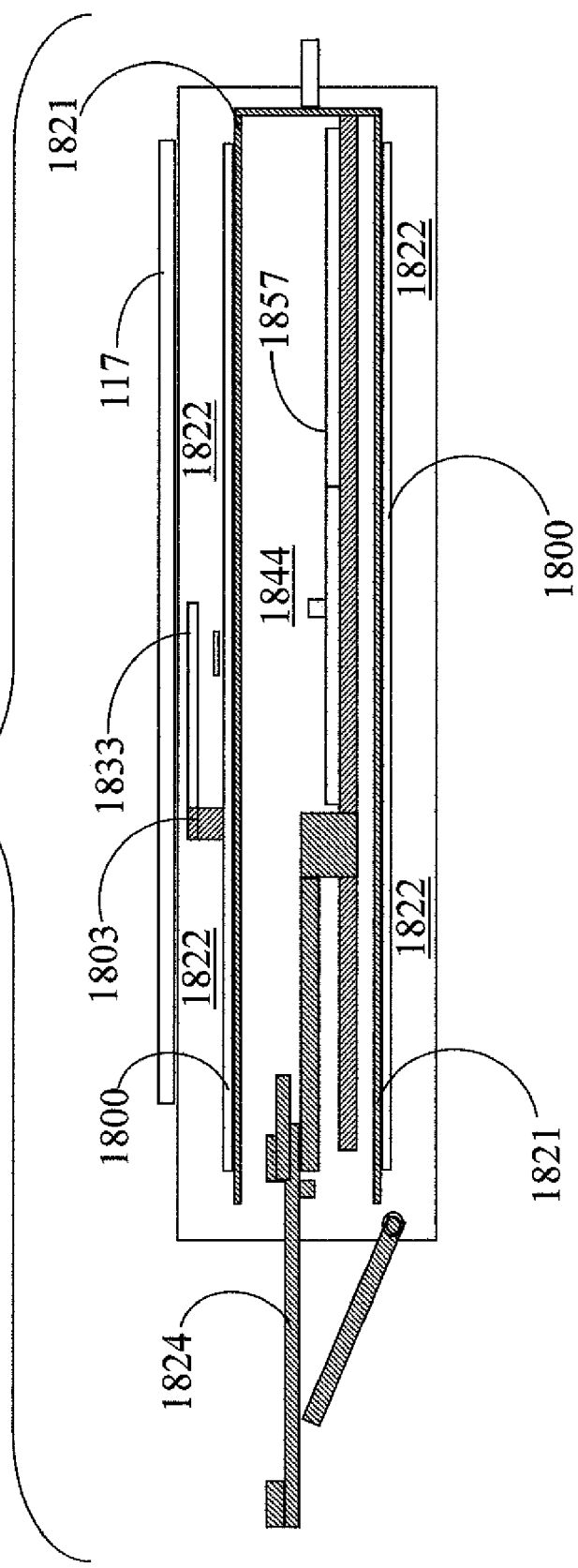
FIG. 18 is a longitudinal schematic elevation view of an optical reader made in accordance with the present invention that includes temperature control and temperature monitoring components for temperature control and optical data correction with an inner incubated chamber.

In another exemplary optical reader 18 shown in FIG. 18, the interior of optical reader 18 may be partitioned into a temperature controlled area 1844 comprising of largely the path of a microplate (not shown) with other areas 1822 within the device not maintaining a controlled temperature. Optical reader 18 includes a sub-enclosure 1821, which may be constructed of heat-conducting sheet metal, such as aluminum, with the heating panels 1800 adhered to sub-enclosure 1821. Sub-enclosure 1821 may completely envelope the path of carrier 1824 that is inside of optical reader 18. Sub-enclosure 1821 may include openings (not shown) to allow light to pass through the enclosure and the microplate and that may perform the functions of optical masks 162, 163, and 164 of optical reader 10 of FIGS. 1 and 2 and may in fact replace the masks altogether. Sub-enclosure 1821 may envelope only the path of the microplate before and after the optics. Those skilled in the art will readily appreciate that components of optical reader 18 of FIG. 18 not particularly described may be the same as or similar to corresponding respective components of either of optical readers 10, 14 and any alternatives described herein or would be apparent to skilled artisans implementing the novel teachings disclosed herein.

The temperature manipulated within optical reader 18 of FIG. 18 may be monitored by MCB 1857 with one or more temperature sensors, such as a model 5665 thermistor Thermal Tab Sensor (Minco, Minneapolis, Minn.), or it may be monitored using one or more non-contact optical temperature sensors 1803 such as a model M50 infrared sensor (Micron Infrared, Inc., Oakland, N.J.). Sensor 1803 may be mounted to one or more interior panels or components inside the temperature-controlled region or sensors may extend into the incubated air space, or sensor 1803 may be integrated into LED array 1833 as taught in FIGS. 14 and 18.

Figure 15:
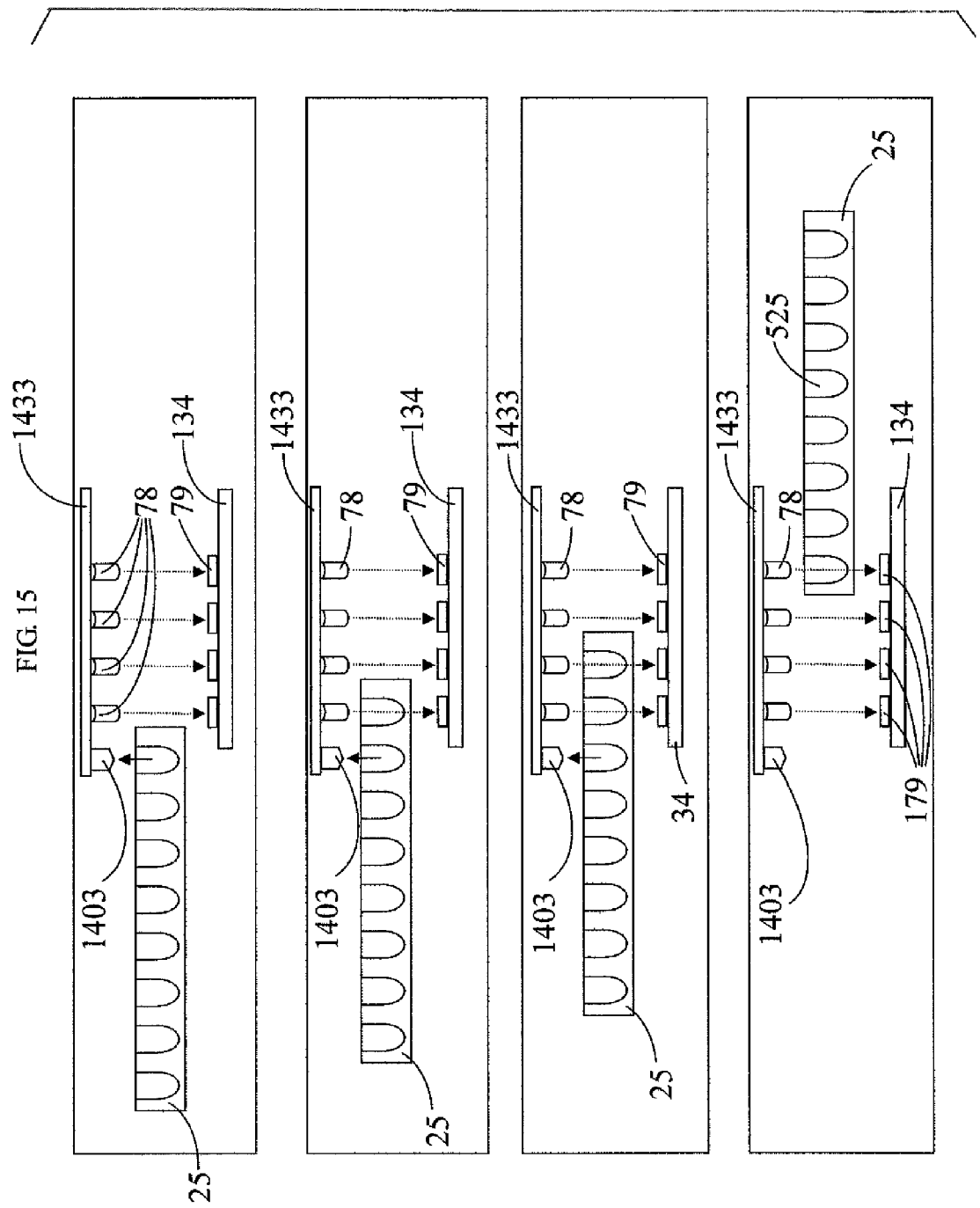
FIG. 15 is a series of longitudinal schematic elevation views illustrating the operation of microplate movement system incorporating temperature measurement and correction.

FIG. 15 illustrates the process of illuminating wells 525 of microplate 25 with LEDs 78 of LED array 1433 and measuring LED light with photodiode array 134 while simultaneously measuring the temperature of the adjacent wells using sensor 1403.

The ability to measure temperatures on a well-to-well basis or by taking several well temperature readings across a give plate or sample-well cluster resolves an important problem not satisfied by known optical readers. It is known in the field of the invention that some chemistry reactions, such as Endotoxin measurements, and their resulting optical readings, are greatly affected by minor temperature deviations on a well-to-well basis. Such deviations are common because interior wells of a microplate heat more slowly than the edge wells of the microplate due to the thermal mass of adjacent wells.

In the art of microplate reading, microplates whose data is adversely affected by a temperature gradient must generally be discarded; however, it is nearly impossible to determine from the optical data alone if a measurable chemical reaction in the microplate wells has caused adverse data or if a temperature gradient has caused adverse data. Existing methods of microplate measurement have failed to address this problem. By using one or more integrated temperature sensors, for example, sensor 1403 on FIG. 14, to measure the temperature of specific wells across the length or width of the microplate, such an adverse temperature gradient can be detected so that the results can be discarded without further wasted analysis of errant data. In another embodiment, a single detector or a plurality of detectors could be used to measure the temperature of each and every microplate well on the microplate. With this additional well-specific temperature data collected, the researcher can then adjust the optical readings based on the temperature readings on a well-to-well basis, independent of whether or not the plate was thermally influenced by the reader.

For example, if a plurality of wells' temperatures were measured, the temperatures could be averaged and if the variation of any individual well from the average temperature were measured outside a limit value programmed into the reader memory, for example, 5% above average or 5% below the average temperature, then a message may be presented on keypad display 117 indicating that there exists an "out of tolerance temperature variation" on the microplate. A tolerance may be programmable through the keypad display 117 so that scientists could devise their own acceptance criteria. Embodiments might incorporate a more sophisticated acceptance criteria based on accepted practices of statistical analysis common to scientists skilled in the arts of microplate data analysis, for example, based on the statistical coefficient of variation (cv %) for a set of temperature measurements. Alternatively, the temperature measurements could be presented as raw data along with the optical measurements so that the scientist could make their own comparison to determine the affect of temperature on optical data and set their own acceptance criteria for temperature variations.

For example, the temperature of all of the wells could be measured and averaged mathematically. Each well temperature could then be compared to the average and the optical reading factored up or down based on the individual well temperature relative to the average. That is, if a well is 10% warmer than average, and the chemistry is known to increase its optical density as a result of increased temperature, the scientist might reduce the optical reading by 10% as a temperature-based correction. It is likely that different temperature sensitive experiments would have unique mathematical corrections based on the effect of well-specific temperature. Those skilled in the art of research using microplates could determine this correction factor or relationship experimentally and then deploy the correction to the measured optical data.

Figure 3:
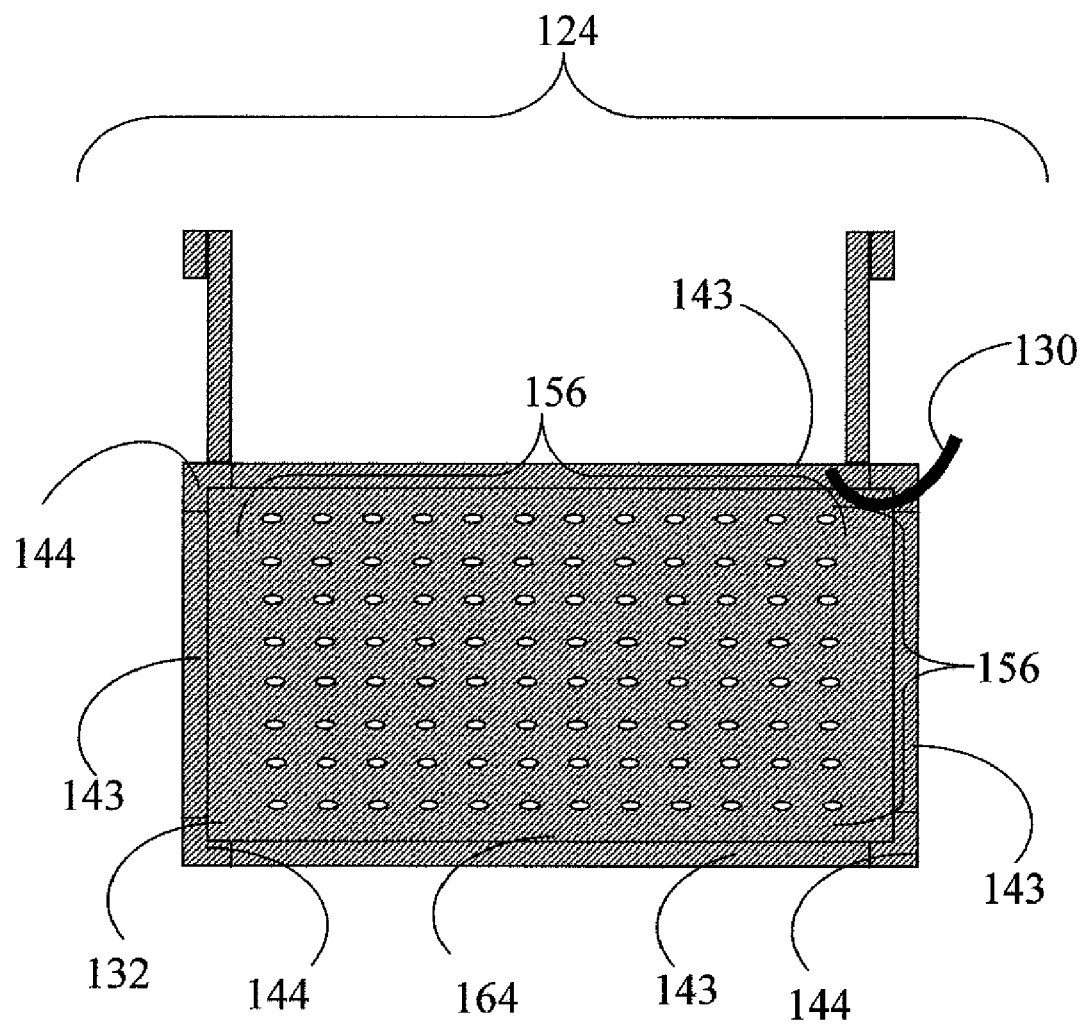
FIG. 3 is an enlarged plan view of the microplate carrier of FIGS. 1 and 2 having an integrated mask.
Figure 4:
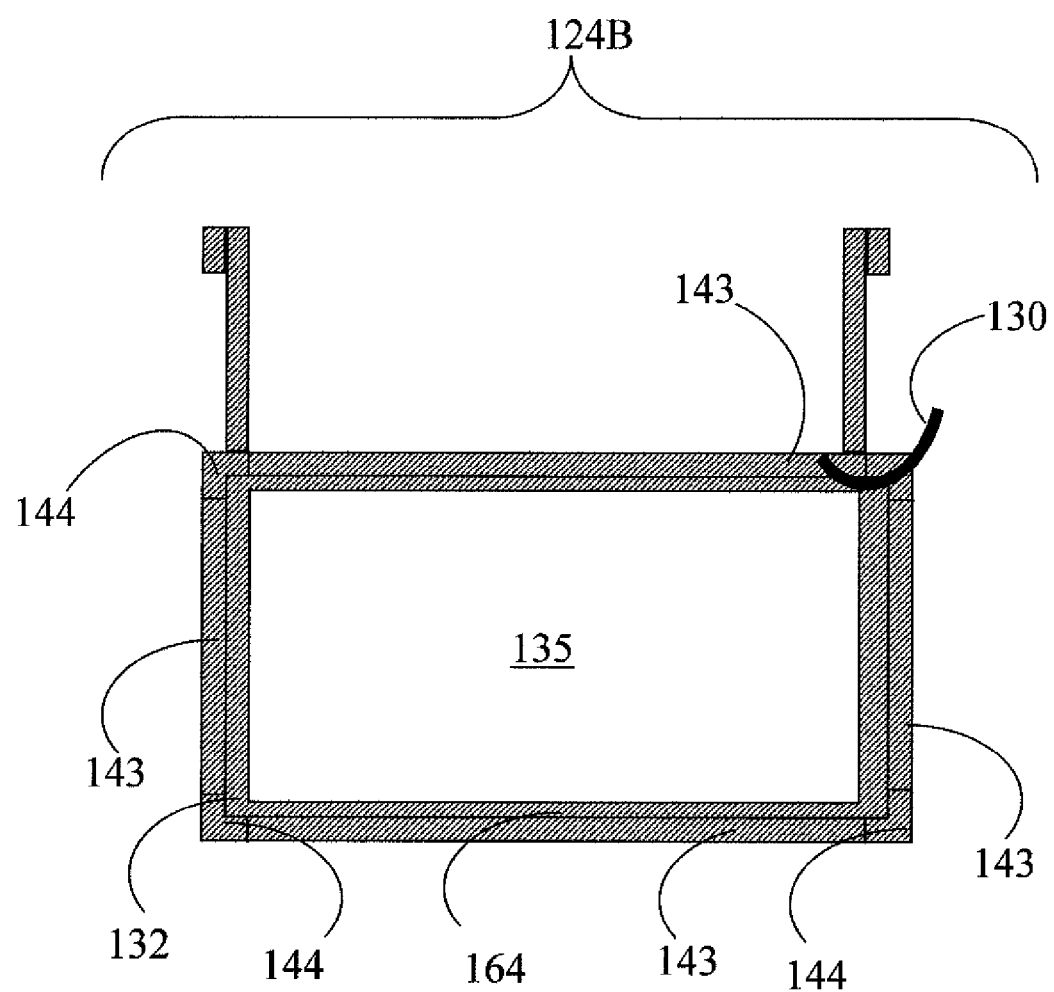
FIG. 4 is an enlarged plan view of an alternative carrier not having an integrated mask.

Returning to FIG. 1, carrier 124 is a frame of sturdy material (sheet or machined metal such as aluminum or sturdy plastic) with open areas 156 (FIG. 2) to allow light to pass from the LED array 133 through microplate 25, to photodiode array 134, without interference. In an alternative carrier 124B shown in FIG. 4, the carrier can be open in its entirety. As shown in FIGS. 2 and 3, carrier 124 can be largely opaque with holes 156 directly beneath the microplate 25 wells to allow passage of LED light only through the bottom of each microplate well.

As shown in FIG. 2, fixed microplate holding points are located on three corners 144 of carrier 124 with a spring member 130 on the fourth corner 139. Spring member 130 pulls away from microplate 25 (not shown) as carrier 124 passes out through the door 121 opening and springs back to apply force to microplate 25 as carrier 24 moves into the chamber. In this example, spring member 130 is a ribbon of mild spring steel, preferably stainless steel, bent as shown in FIG. 3. End 1301 of the spring member 130 is attached to carrier 124, by a screw or similar fastener, with opposite end 1302 floating in space unless held against the door opening 1201 when carrier 124 has moved outside optical reader 10 (FIG. 2) or unless holding microplate 25 in place (not shown). In alternative embodiments, spring member 130 could be, among other things, a rigid arm that pivots on a fixed axis with a radial spring providing the force to hold a microplate in place.

By holding microplate 25 on its corners, a mechanical microplate gripping and positioning device has access to the long or short sides 143 of microplate 25 allowing for compatibility with various brands of microplate handling robotic devices, such as the Flash-6X SSI Robotics model (Shoreview, Minn.) or the Twister II Plate Handler from Caliper Life Sciences (Hopkinton, Mass.). Another capability facilitated by the open sides 143 of carrier 124 would be the ability to use a hand-held barcode scanner (not shown) to read barcode labels (not shown) on a side of microplate 25 or to add a small barcode scanner to optical reader 10 to allow reading of a barcode label adhered on any of the four sides of microplate 25 to identify a particular microplate relative to other microplates. In another embodiment, a different identity reading device, such as a radio frequency identification (RFID) tag reader (not shown) may be used. Scientist familiar with the art of microplate reading will also be familiar with the techniques and methods of identifying and monitoring a series of microplates using barcode scanners and labels.

In the exemplary optical reader 10 (FIG. 1), carrier 124 features a small metal tab 145 that protrudes beneath carrier 124 and passes through optical sensor 146 as a means of determining the position of carrier 124 relative to LED array 133 and Photodiode array 134. In this embodiment, optical sensor 146 may be model QVE11233 sensor from Fairchild Semiconductor (South Portland, Me.) or similar, attached to photodiode array 134 and activated by metal tab 145 attached to carrier 124. During manufacture, the distance from sensor 146 to the first row of the microplate 25 is input into electronic memory so that each time carrier 124 activates sensor 146, the MCB 157 can send the command for motor 147 to move carrier 124, and therefore the samples, into precise alignment relative to the LED array 133. In another embodiment, MCB 157 may determine carrier 124 position directly from the built-in feedback capability of stepper motor 147 without the need for sensor 146 or sensor tab 145.

In the example of optical reader 10 of FIGS. 1 and 2, carrier 124 slides along two metal rails 128 to move smoothly in and out of optical reader 10 while maintaining a precise alignment with the optics. There are several sources and styles of rails 128 and rail materials and methods to attach them to carrier 124, such as those offered by Nook Industries (Cleveland, Ohio) or Danaher Motion (Wood Dale, Ill.). In one embodiment, a bearing block 150 wraps around the rail and attaches to carrier 124 via two screws, rivets, or equivalent fasteners.

Carrier 124 is moved along the rails 128 via attachment clamp 161 to a toothed belt 126, as available through Belt Corporation of America (Cumming, Ga.). Belt 126 is powered by a small toothed gear 149 on stepper motor 147, such as part number 208-17-01 or similar available from Lin Engineering (Santa Clara, Calif.). Belt 126 should be maintained at the proper tension via a spring loaded idler pulley 148 at the end-loop of belt 126 opposite motor 147.

In alternative embodiments, optical readers made in accordance with the present invention move a microplate (or other sample-well cluster) between an array of light sources and a detector, take readings in a single pass, and eject the microplate out a second door at the other end of the optical reader, for example, conveyor belt style, similar to a pizza in an automated commercial pizza oven.

Other alternative optical readers, such as optical reader 16 of FIG. 16, include a differently shaped carrier, such as carrier 1624, to hold an alternative sample vessel, such as vessel 1625, for example, individual removable wells or strips of wells, such as a 1-by-8 well strip or a 1-by-12 well strip, instead of an entire microplate. In this example, LED array 1633 is a 1-by-4 one-dimensional arrangement that can read the sample holder at a plurality of wavelengths in a single pass through the optics. Other embodiments could hold other types of sample vessels, such as test tubes, microplate slides or cuvettes. It is noted that as used herein and in the appended claims, the term "sample well" and like terms denote the space where a sample is placed during reading. Consequently, structures other than microplates, such as test tubes and cuvettes, are considered to provide sample wells. As those skilled in the art will understand, all other components of optical reader 16 not explicitly described can be the same as or similar to the corresponding components of other optical readers shown and described herein.

FIG. 17 illustrates other embodiments of optical and mechanical sub-assemblies 17A and 17B. Utilizing the teachings of FIG. 17 and FIGS. 1 and 2 and other teachings herein, one skilled in the art could build an optical reader around multi-wavelength sub-assemblies 17A or 17B. Herein, LED array 1733A may be made to move by motor 1748A in a direction perpendicular to microplate 25 (carrier not shown), which is conversely moved by motor 1747A, to read all the wells on the microplate and measure the temperature of all the wells on the plate using thermal sensor 1703. Because microplate 25 and LED array 1733A move independently relative to one another on rails 1728A and 1728AA, different geometry microplates, for example, 96-well, 384-well, 24-well, 48-well, etc., microplates plates may be read on the same device through alternative movement commands without hardware changes. As a result, this embodiment would enjoy a similar 3 to 4 fold improvement in throughput performance when compared to existing single channel microplate readers.

Similarly, a second exemplary LED array 1733B shown in FIG. 17 may be fixed inside an optical reader in alignment with a corresponding photodiode array (not shown), but in this example microplate 25 may be moved on perpendicularly mounted rails 1728 to allow the plate to move in two directions between LED array 1733B and photodiode array (not shown, obscured beneath LED Array 1733B) allowing all the sample wells of microplate 25 to be read at a plurality or wavelengths in one pass while simultaneously measuring its temperature via sensor 1703. Similar to configuration 17A, because microplate 25 moves in two dimensions, different geometry microplates, for example, 96-well, 384-well, 24-well, 48-well, etc., may be read on the same device through alternative movement commands and without hardware changes. As a result, this embodiment too would enjoy a similar 3 to 4 fold improvement in throughput performance when compared to existing single channel microplate readers.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An optical reader for acquiring optical data corresponding to each of a plurality of sample wells of a cluster of sample wells, the optical reader comprising:
   an illuminating array including a plurality of light sources of predetermined differing-wavelength outputs;
   a detector operatively configured and located to detect light from said predetermined differing-wavelength outputs from said illuminating array;
   a reading region located between said illuminating array and said detector during operation of the optical reader; and
   a controller operatively configured to control movement of one, the other, or both, of said illuminating array and the cluster of sample wells and to control pulsing of said plurality of light sources so as to illuminate simultaneously corresponding respective ones of the plurality of sample wells with said predetermined differing-wavelength outputs.

2. An optical reader according to claim 1, wherein said plurality of light sources includes a plurality of differing output color light emitting diodes arranged in a planar array.

3. An optical reader according to claim 1, wherein said illuminating array and said detector are configured to allow a user to obtain light-absorbance data during use of the optical reader.

4. An optical reader according to claim 1, wherein the cluster of sample wells is defined by a microplate.

5. An optical reader according to claim 1, wherein said plurality of light sources further includes a plurality of filters corresponding respectively to said plurality of light sources, said plurality of light filters working in conjunction with said plurality of light sources to provide said predetermined differing wavelength outputs.

6. An optical reader according to claim 1, wherein said plurality of light sources includes at least three light sources having corresponding respective output colors differing from one another.

7. An optical reader according to claim 6, wherein said controller is operatively configured to simultaneously pulse said at least three light sources when said at least three light sources are located proximate corresponding respective differing ones of the plurality of sample wells.

8. An optical reader according to claim 1, said plurality of light sources are arranged into a plurality of sub-arrays each containing only ones of said plurality of light sources of a common wavelength output, said common wavelength output differing as between ones of said plurality of sub-arrays.

9. An optical reader according to claim 8, wherein each of said plurality of sub-arrays is a one-dimensional array.

10. An optical reader according to claim 8, wherein each of said plurality of sub-arrays is a multi-dimensional array.

11. An optical reader according to claim 10, wherein the optical reader is configured for acquiring optical data regarding sample wells of microplates having differing well spacings and at least one of said sub-arrays contains ones of said plurality of light sources arranged to accommodate the differing well spacings.

12. An optical reader according to claim 8, wherein the plurality of sample wells are arranged in rows in the cluster and each of said plurality of sub-arrays includes at least a number of said plurality of light sources that corresponds to the number of the sample wells in any of the rows in the cluster.

13. An optical reader according to claim 8, wherein said plurality of sub-arrays includes at least three sub-arrays having corresponding respective color outputs differing from one another, said controller operatively configured to simultaneously pulse at least one of said plurality of light sources in each of said at least three sub-arrays when each of said at least one of said plurality of light sources is located proximate a corresponding one of the plurality of sample wells.

14. An optical reader according to claim 13, wherein said controller is operatively configured to simultaneously pulse multiple ones of said plurality of light sources in each of said at least three sub-arrays when each of said multiple ones of said plurality of light sources is located proximate a corresponding one of the plurality of sample wells.

15. An optical reader according to claim 1, wherein said plurality of light sources are arranged into a first arrangement and said detector comprises an array of photosensors arranged into a second arrangement substantially the same as said first arrangement.

16. A method of acquiring optical data corresponding to each of a plurality of sample wells of a cluster of sample wells, the method comprising:
   positioning the cluster of sample wells in a reading region located between a light-source array and a light detector during reading, the light-source array including at least two light sources having differing output wavelengths and located relative to one another so that when the cluster is in a reading position within the reading region, the at least two light sources are located proximate corresponding respective ones of the plurality of sample wells;
   when the at least two light sources are located adjacent corresponding respective ones of the plurality of sample wells, simultaneously pulsing the at least two light sources so as to direct light toward a first side of the cluster;
   in coordination with the simultaneous pulsing, sensing via the detector, from a second side of the cluster opposite the first side, light from the at least two light sources that passed through the corresponding respective ones of the plurality of wells; and
   acquiring optical data corresponding to the light detected by the detector.

17. A method according to claim 16, wherein the light-source array includes three light sources having differing output wavelengths and located relative to one another so that when the cluster is in a reading position within the reading region, the three light sources are located proximate corresponding respective ones of the plurality of sample wells and the method includes, when the three light sources are located adjacent corresponding respective ones of the plurality of sample wells, simultaneously pulsing the three sources so as to direct light toward the first side of the cluster.

18. A method according to claim 16, wherein the light-source array includes at least two sub-arrays each containing a plurality of like-wavelength output light sources having a primary wavelength, the primary wavelength differing as between the at least two sub-arrays, the method including, when ones of the plurality of like-wavelength output light sources in each of the at least two sub-arrays are located proximate corresponding respective ones of the plurality of wells, simultaneously pulsing ones of the plurality of like-wavelength output light sources in all of the at least two sub-arrays.

19. A method according to claim 18, wherein each of the at least two sub-arrays is a linear array and the method further includes pulsing alternating ones of the plurality of like-wavelength output light sources in each linear array.

20. A method according to claim 16, wherein said acquiring of optical data includes acquiring light-absorbance data.

* * * * *